US010231727B2

(12) United States Patent
Sutherland et al.

(10) Patent No.: US 10,231,727 B2
(45) Date of Patent: *Mar. 19, 2019

(54) PLICATION LOCK DELIVERY SYSTEM AND METHOD OF USE THEREOF

(71) Applicant: Mitralign, Inc., Tewksbury, MA (US)

(72) Inventors: Michael Sutherland, Pelham, NH (US); Jonathan Goodwin, Nashua, NH (US); Megan Holmes, Nashua, NH (US); Christopher Lee, Tewksbury, MA (US); Adam Vigneault, Newbury, MA (US); John DePiano, Burlington, MA (US); James Sellers, Eliot, ME (US)

(73) Assignee: MITRALIGN, INC., Tewksbury, MA (US)

( * ) Notice: Subject to any disclaimer, the term of this patent is extended or adjusted under 35 U.S.C. 154(b) by 373 days.

This patent is subject to a terminal disclaimer.

(21) Appl. No.: 14/965,304

(22) Filed: Dec. 10, 2015

(65) Prior Publication Data

US 2016/0128689 A1 May 12, 2016

Related U.S. Application Data

(63) Continuation of application No. 14/039,779, filed on Sep. 27, 2013, now Pat. No. 9,216,018.
(Continued)

(51) Int. Cl.
*A61B 17/04* (2006.01)
*A61F 2/24* (2006.01)
(Continued)

(52) U.S. Cl.
CPC ...... *A61B 17/0469* (2013.01); *A61B 17/0401* (2013.01); *A61B 17/0485* (2013.01);
(Continued)

(58) Field of Classification Search
CPC ............... A61F 2/2445; A61F 2/2451; A61F 2002/0817–2002/0841; A61B 17/0401;
(Continued)

(56) References Cited

U.S. PATENT DOCUMENTS 1,518,523 A * 12/1924 Kubik ................ D06F 53/00
24/136 A
3,572,804 A * 3/1971 Nims ................ F16G 11/048
24/115 L
(Continued)

FOREIGN PATENT DOCUMENTS

CN 101056587 10/2007
EP 0 643 945 3/1995
(Continued)

*Primary Examiner* — Ryan J Severson
*Assistant Examiner* — Charles Wei
(74) *Attorney, Agent, or Firm* — Leason ellis LLP

(57) ABSTRACT

A plication lock delivery system that enables a suture lock assembly to be delivered percutaneouly. The plication lock delivery system comprises a lock assembly that secures sutures in place, a control assembly that allows a clinician to engage a suture to a suture lock assembly, apply tension to the sutures to cause tissue plication, and deploy the lock assembly, and a catheter assembly. This plication lock delivery system can be used to repair mitral regurgitation percutaneouly or in an open-heart surgery.

6 Claims, 13 Drawing Sheets

Related U.S. Application Data

(60) Provisional application No. 61/707,940, filed on Sep. 29, 2012.

(51) Int. Cl.
*A61B 17/00* (2006.01)
*A61B 17/29* (2006.01)
*A61B 90/00* (2016.01)

(52) U.S. Cl.
CPC .............. *A61B 17/0487* (2013.01); *A61B 2017/00243* (2013.01); *A61B 2017/0406* (2013.01); *A61B 2017/0409* (2013.01); *A61B 2017/0417* (2013.01); *A61B 2017/0419* (2013.01); *A61B 2017/0464* (2013.01); *A61B 2017/0488* (2013.01); *A61B 2017/0496* (2013.01); *A61B 2017/2923* (2013.01); *A61B 2090/0811* (2016.02); *A61F 2/2451* (2013.01)

(58) Field of Classification Search
CPC ............ A61B 17/0485; A61B 17/0487; A61B 17/8875; A61B 17/8886; A61B 2017/0409; A61B 2017/0414; A61B 2017/0427; A61B 2017/0438; A61B 2017/0445; A61B 2017/0446; A61B 2017/0448; A61B 2017/0458; A61B 2017/048; A61B 2017/0488; A61B 2017/0496; A61B 2017/00243
See application file for complete search history.

(56) References Cited

U.S. PATENT DOCUMENTS

| | | | |
|---|---|---|---|
| 3,814,347 A * | 6/1974 | Moren, Jr. | B65H 75/28 242/125.1 |
| 5,693,059 A | 12/1997 | Yoon | |
| 5,927,637 A * | 7/1999 | Gerhards | B65H 75/28 242/125.1 |
| 6,718,985 B2 | 4/2004 | Hlavka et al. | |
| 7,037,334 B1 | 5/2006 | Hlavka et al. | |
| 7,166,127 B2 | 1/2007 | Spence et al. | |
| 7,431,726 B2 | 10/2008 | Spence et al. | |
| 7,713,278 B2 | 5/2010 | Hess et al. | |
| 7,824,443 B2 * | 11/2010 | Salahieh | A61F 2/2439 623/2.11 |
| 8,142,493 B2 | 3/2012 | Spence et al. | |
| 8,202,315 B2 | 6/2012 | Hlavka et al. | |
| 8,460,371 B2 | 6/2013 | Hlavka et al. | |
| 8,845,723 B2 | 9/2014 | Spence et al. | |
| 8,864,822 B2 | 10/2014 | Spence et al. | |
| 8,911,461 B2 | 12/2014 | Traynor et al. | |
| 8,945,211 B2 | 2/2015 | Sugimoto | |
| 8,951,285 B2 | 2/2015 | Sugimoto et al. | |
| 8,951,286 B2 | 2/2015 | Sugimoto et al. | |
| 8,968,335 B2 | 3/2015 | Robinson et al. | |
| 8,979,923 B2 | 3/2015 | Spence et al. | |
| 9,216,018 B2 * | 12/2015 | Sutherland | A61B 17/0401 |
| 2004/0133239 A1 | 7/2004 | Singhatat | |
| 2006/0106422 A1 | 5/2006 | Del Rio et al. | |
| 2006/0276825 A1 * | 12/2006 | Mitelberg | A61B 17/12022 606/200 |
| 2007/0276437 A1 * | 11/2007 | Call | A61B 17/0487 606/232 |
| 2008/0228165 A1 * | 9/2008 | Spence | A61B 17/00234 604/510 |
| 2008/0228265 A1 | 9/2008 | Spence et al. | |
| 2008/0228267 A1 | 9/2008 | Spence et al. | |
| 2009/0076547 A1 | 3/2009 | Sugimoto et al. | |
| 2009/0163934 A1 | 6/2009 | Raschdorf et al. | |
| 2009/0240206 A1 | 9/2009 | Lunn et al. | |
| 2010/0016655 A1 | 1/2010 | Annest et al. | |
| 2011/0087247 A1 * | 4/2011 | Fung | A61B 17/0469 606/148 |
| 2012/0109155 A1 * | 5/2012 | Robinson | A61B 17/0401 606/139 |

FOREIGN PATENT DOCUMENTS

| | | |
|---|---|---|
| EP | 2 446 831 | 5/2012 |
| WO | WO 97/30649 | 8/1997 |
| WO | WO2004/098701 | 11/2004 |

* cited by examiner

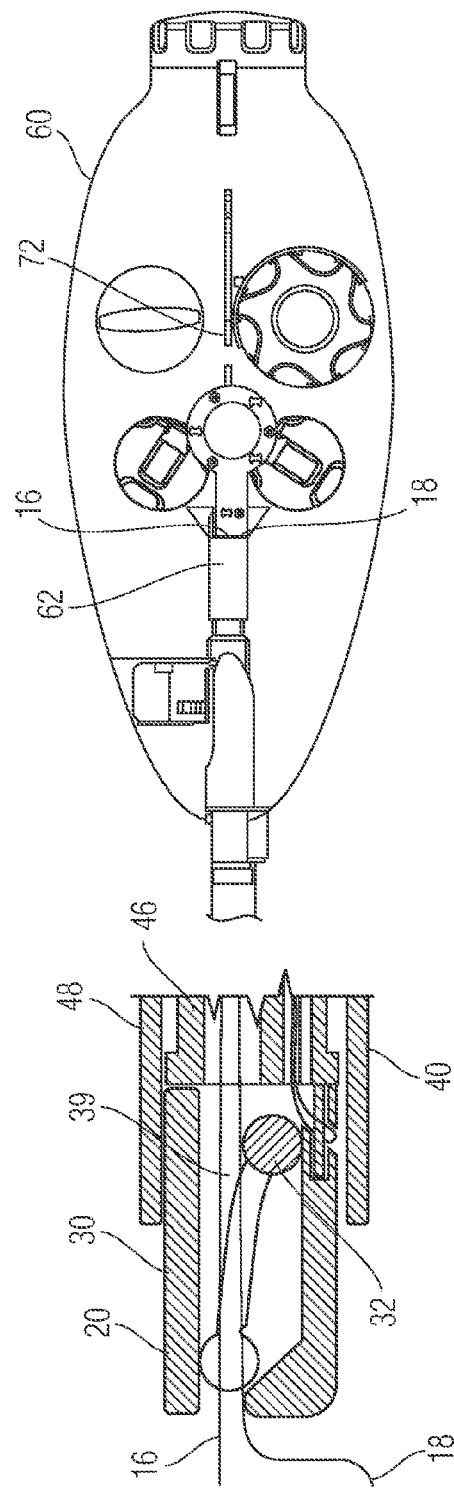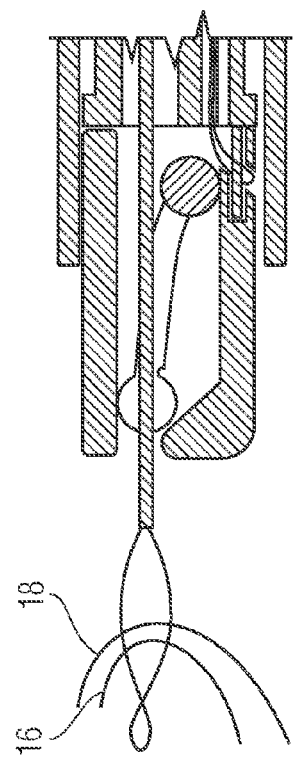

PLICATION LOCK DELIVERY SYSTEM AND METHOD OF USE THEREOF

CROSS-REFERENCE TO RELATED APPLICATION

The present application is a continuation of U.S. patent application Ser. No. 14/039,779, filed Sep. 27, 2013, which claims priority to U.S. patent application Ser. No. 61/707,940, filed Sep. 29, 2012, which are incorporated by reference as if expressly set forth in their respective entireties herein.

TECHNICAL FIELD

The present teachings generally relate to lock assemblies, for example, used in catheter-based surgical procedures. The present teachings also relate to plication lock delivery systems and methods of using such plication lock delivery systems to deliver and deploy a lock assembly of the present teachings to, for example, secure one or more tensioning members.

BACKGROUND

Catheter-based surgical procedures can be used to repair tissues, such as a defective mitral valve. One such catheter-based surgical procedure, commonly referred to as annuloplasty, reduces the length of a posterior mitral valve leaflet through one or more plications. Specifically, anchors are secured at a plurality of locations distributed around the annulus near the posterior leaflet of a mitral valve. Each anchor has a suture coupled thereto. The sutures are collectively gathered and pulled tight. As the sutures are pulled, the tissue between each pair of adjacent anchors is plicated, thereby shortening the length of the annulus and drawing the posterior leaflet toward the anterior leaflet.

During a surgical procedure, the sutures for each of the anchors extend to an incision site through a catheter. To preserve the plications, the sutures must be secured against movement. Because the procedures are catheter-based, suture locks are typically used because of the small diameter of the catheter.

There is generally a need for an improved lock to secure one or more tensioning members, such as sutures, against relative movement during and after a catheter-based surgical procedure and an improved plication lock delivery system to deliver the improved lock.

SUMMARY

One aspect of the present teachings provides a lock delivery system for delivering a lock assembly percutaneously. In various embodiments, a lock delivery system comprises a lock assembly. In some embodiments, the lock assembly is configured to secure at least one suture. In various embodiments, a lock delivery system comprises a catheter assembly. In some embodiments, the catheter assembly comprises a distal end and a proximal end, wherein the distal end of the catheter assembly is configured to connect the lock assembly. In various embodiments, a lock delivery system comprises a control assembly. In some embodiments, the control assembly is configured to connect the proximal end of the catheter assembly. In some embodiments, the control assembly is configured to apply tension to at least one suture. In some embodiments, the control assembly is configured to activate the securing of at least one suture to the lock assembly. In some embodiments, the control assembly is configured to release the lock assembly.

Another aspect of the present teachings provides a plication lock delivery system, for example, for creating a tissue plication. In various embodiments, a plication lock delivery system comprises a lock assembly. In some embodiment, the lock assembly comprises a lock body and a lock pin. In certain embodiments, the lock body has a central lumen configured to retain the lock pin and to have at least two sutures disposed within the central lumen. In various embodiments, a plication lock delivery system further comprises a catheter assembly. In some embodiments, the catheter assembly comprises an outer sheath and an inner catheter. In certain embodiments, the inner catheter has a distal end, a proximal end, and a central lumen. In particular embodiments, the distal end of the inner catheter is configured to connect the lock body. In particular embodiments, the central lumen of an inner catheter is configured to have the two sutures disposed within. In particular embodiments, the outer sheath of a catheter assembly has a distal end and a proximal end. In particular embodiments, the distal end of an outer sheath is configured to contact the lock pin. In various embodiments, a plication lock delivery system also comprises a control assembly. In some embodiments, the control assembly comprises a first suture tension mechanism configured to apply tension to one suture. In some embodiments, the control assembly comprises a second suture tension mechanism configured to apply tension to the second suture. In some embodiments, the control assembly comprises a lock deploy-and-release mechanism configured to secure the two sutures to the lock assembly and to release the lock assembly inside the body. In some embodiments, the control assembly connects the proximal ends of the outer sheath and inner catheter.

Another aspect of the present teachings provides a control assembly of a plication lock delivery system. In various embodiments, a control assembly comprises a housing that includes at least one of a suture tension mechanism, a tissue plication mechanism, and a lock deploy-and-release mechanism. In some embodiments, a suture tension mechanism is configured to secure and apply tension to one suture. In some embodiments, a tissue plication mechanism is configured to secure and apply tension to another suture. In some embodiments, a lock deploy-and-release mechanism is configured to secure the two sutures to a lock assembly and to release the lock assembly from the control assembly.

Another aspect of the present teachings provides a method of delivering a lock assembly percutaneusly. In various embodiments, the method includes providing a lock delivery system with a lock assembly, a catheter assembly comprising a distal end and a proximal end, and a control assembly. In some embodiment, the lock assembly is configured to secure at least one suture. In other embodiments, the distal end of the catheter assembly is configured to connect the lock assembly, and the control assembly is configured to connect the proximal end of the catheter assembly, to apply tension to the at least one suture, to activate the securing of the suture to the lock assembly, and to release the lock assembly. In other embodiments, the method further includes extending the at least one suture through the lock assembly, extending the at least one suture from the distal end to the proximal end of the catheter assembly, joining the at least one suture to the control assembly, applying tension to the at least one suture, secure the tensioned suture to the lock assembly, and releasing the lock assembly from the catheter assembly.

Another aspect of the present teachings provides a method of plicating a tissue and securing the tissue plication with a lock assembly percutaneusly. In various embodiment, the method comprises providing a plication lock delivery system of the present teachings, for example, including a lock assembly, a catheter assembly comprising an outer sheath and an inner catheter, and a control assembly. In some embodiments, the lock assembly comprises a lock body and a lock pin, wherein the lock body has a central lumen configured to retain the lock pin and have two sutures disposed within. In other embodiments, the inner catheter has a distal end, a proximal end, and a central lumen, wherein the distal end of the inner catheter is configured to connect the lock body, and the central lumen is configured to have the two sutures disposed within, and the outer sheath has a distal end configured to contact the lock pin and a proximal end. In yet other embodiments, the control assembly connects the proximal ends of the outer sheath and inner catheter and comprises a first suture tension mechanism configured to apply tension to one suture, a second suture tension mechanism configured to apply tension to another suture, and a lock deploy-and-release mechanism configured to secure the two sutures to the lock assembly and to release the lock assembly inside the body. In yet other embodiments, the method further comprises extending the two sutures through the lock assembly. In yet other embodiments, the method further comprises extending the two sutures from the distal end to the proximal end of the catheter assembly. In yet other embodiments, the method further comprises applying tension to one suture with the first suture tension mechanism of the control assembly. In yet other embodiments, the method further comprises applying tension to the another suture with the second suture tension mechanism of the control assembly. In yet other embodiments, the method further comprises securing the two sutures to the lock assembly with the lock deploy-and-release mechanism of the control assembly. In yet other embodiments, the method further comprises releasing said lock assembly from the catheter assembly.

BRIEF DESCRIPTION OF THE DRAWING FIGURES

FIG. 7b is a cross-sectional view of an exemplary plication lock delivery system in accordance with the present teachings;

FIG. 8a is a top plan view of an exemplary control assembly of a plication lock delivery system in accordance with the present teachings;

FIG. 8b is a cross-sectional view of an exemplary plication lock delivery system in accordance with the present teachings;

DETAILED DESCRIPTION OF CERTAIN EMBODIMENTS

Figure 1:
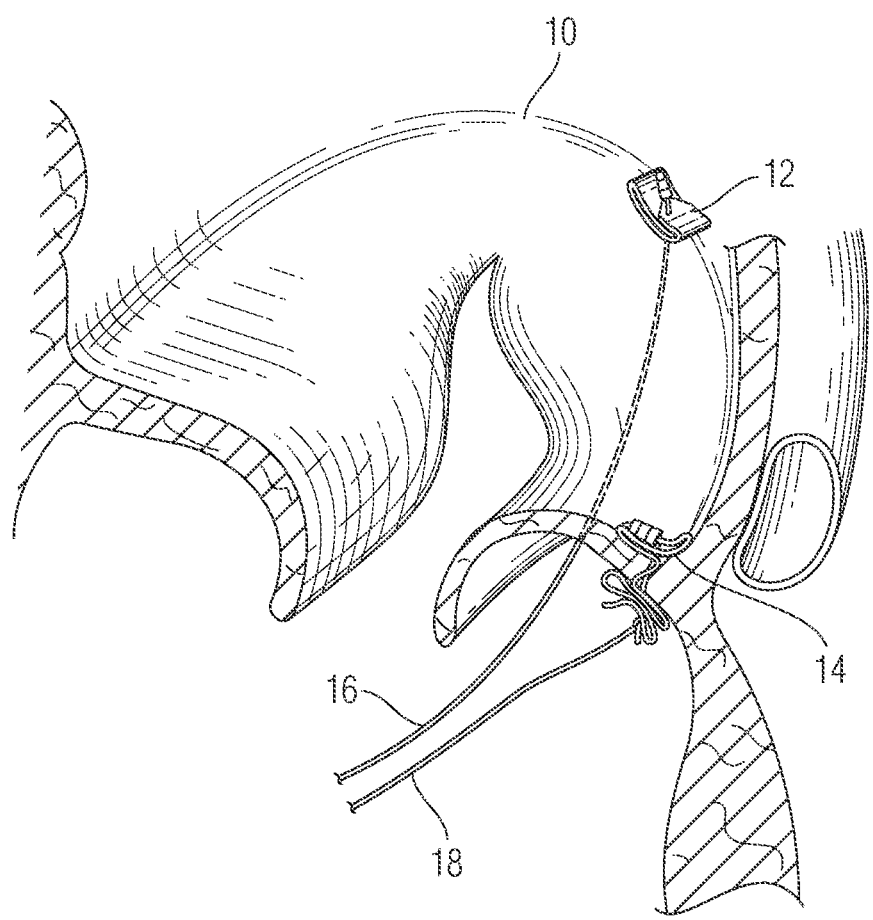
FIG. 1 is a perspective view of two exemplary pledgets deployed at a mitral valve annulus in accordance with the present teachings.

Certain specific details are set forth in the following description and Figures to provide an understanding of various embodiments of the present teachings. Those of ordinary skill in the relevant art will understand that they can practice other embodiments of the present teachings without one or more of the details described below. Thus, it is not the intention of the Applicants to restrict or in any way limit the scope of the appended claims to such details. While various processes are described with reference to steps and sequences in the following disclosure, the steps and sequences of steps should not be taken as required to practice all embodiments of the present teachings.

As used herein, the terms "subject" and "patient" refer to an animal, such as a mammal, such as a livestock, a pet, and, preferably, a human. Specific examples of "subjects" and "patients" include, but are not limited to, individuals requiring medical assistance and, in particular, requiring treatment for heart failure or valve dysfunction.

As used herein, the term "lumen" means a canal, duct, generally tubular space or cavity in the body of a subject, including veins, arteries, blood vessels, capillaries, intestines, and the like.

As used herein, the term "proximal" means closest to the operator (less into the body) and "distal" shall mean furthest from the operator (further into the body). In positioning a medical device from a downstream access point, distal is more upstream and proximal is more downstream.

As used herein, the term "suture" means a tensioning member which can take forms other than a suture material, such as a cable or any other small diameter, flexible, semi-rigid or rigid material having a suitably high tensile strength for the intended use. It will be readily appreciated that while the embodiments of the present teachings as described herein sometimes refer to as a suture lock, the present teachings contemplate that the suture lock can also be used with tensioning members other than sutures.

As used herein, the term "wire" can be a strand, a cord, a fiber, a yarn, a filament, a cable, a thread, or the like, and these terms may be used interchangeably.

Unless otherwise specified, all numbers expressing quantities, measurements, and other properties or parameters used herein are to be understood as being modified in all instances by the term "about." Accordingly, unless otherwise indicated, it should be understood that the numerical parameters set forth in the following specification and attached claims are approximations. At the very least, and not as an attempt to limit the application of the doctrine of equivalents to the scope of the claims, numerical parameters should be read in light of the number of reported significant digits and the application of ordinary rounding techniques.

The present teachings provide a plication lock delivery system (100). For example, a plication lock delivery system can be used to deliver a suture lock device or assembly (20), for example, percutaneouly, into a patient's body where tension can be applied to a suture by the delivery system, causing tissue plication. In some embodiments, the lock assembly (20) secures the sutures in place.

Various embodiments of the present teachings include a control device or assembly (60). In some embodiments, the control assembly allows a clinician to engage a suture to a suture lock assembly (20). In some embodiments, the control assembly allows a clinician to apply tension to the suture to cause tissue plication. In some embodiments, the control assembly allows a clinician to deploy the lock assembly (20). In some embodiments, a clinician conducts at least one of these steps percutaneously. In other embodiments, a clinician conducts at least one of these steps in other minimally invasive approaches or in an open-heart surgery. In various embodiments, the tissue is a mitral valve annulus.

The present teachings also provide a plication lock delivery system. In various embodiments, the plication lock delivery system (100) includes the control assembly (60). In various embodiments, the plication lock delivery system (100) further comprises a catheter assembly (40).

As illustrated in FIG. 1, in various embodiments, two pledgets (12, 14) deployed on a mitral valve annulus (10) with one suture extending from each pledget (12, 14) to the outside of the patient body. For ease of explanation, the term "two sutures" will be used hereinafter, although it should be understood that the term "two sutures" can refer to two ends of the same suture, or two ends of two sutures with the other two ends connected to each other, or two separate sutures. Although pledgets (12, 14) are used to exemplify the present teachings, one skilled in the art should understand that tissue anchors with other shapes, sizes, designs, and materials can also be used. Specifically, tissue anchors embodiments are described in U.S. Pat. No. 6,718,985, entitled "Method and apparatus for catheter-based annuloplasty using local plications," filed May 25, 2001; U.S. Pat. No. 7,037,334, entitled "Method and apparatus for catheter-based annuloplasty using local plications," filed Jul. 18, 2003; U.S. Pat. No. 7,166,127, entitled "Tissue fastening system and methods utilizing magnetic guidance," filed Sep. 24, 2004; U.S. Pat. No. 7,431,726, entitled "Tissue fastening system and methods utilizing magnetic guidance," filed Sep. 24, 2004; U.S. Pat. No. 8,142,493, entitled "Method of heart valve repair," filed Jul. 22, 2008; U.S. Pat. No. 8,202,315, entitled "Catheter-based annuloplasty using ventricularly positioned catheter," filed Aug. 2, 2010; U.S. patent application Ser. No. 10/689,872, entitled "Method and apparatus for catheter-based annuloplasty using local plications," filed Oct. 21, 2003; U.S. patent application Ser. No. 10/948,923, entitled "Tissue fastening systems and methods utilizing magnetic guidance," filed Sep. 24, 2004; U.S. patent application Ser. No. 11/174,951, entitled "Tissue anchor, anchoring system and methods of using the same," filed Jul. 5, 2005; U.S. patent application Ser. No. 11/685,239, entitled "Systems and methods for introducing elements into tissue," filed Mar. 13, 2007; U.S. patent application Ser. No. 11/685,240, entitled "Tissue anchor, anchoring system and methods, and devices," filed Mar. 13, 2007; U.S. patent application Ser. No. 11/685,242, entitled "Devices and methods for introducing elements into tissue," filed Mar. 13, 2007; U.S. patent application Ser. No. 12/273,670, entitled "Tissue anchor and anchoring system," filed Nov. 19, 2008; and U.S. patent application Ser. No. 12/557,655, entitled "Tissue plication device and method for its use," filed Sep. 11, 2009. Each of the above mentioned patents and patent applications is incorporated herein by reference in its entirety.

According to various embodiments of the present teachings, a tissue plication and lock procedure starts by conditioning a plication lock delivery system (100), which can include the lock assembly (20), the catheter structure or assembly (40), and the control assembly (60), into a pre-load configuration. For example, in the pre-load configuration, a catheter assembly (40) engages the lock assembly (20) at its distal end (42) and connects to the control assembly (60) at its proximal end (44); an inner catheter (46) of the catheter assembly (40) is compressed by an outer sheath (48); and the outer sheath (48) is in tension by the inner catheter (46). Without being limited to any specific theory, the pre-load configuration can prevent the inner catheter (46) from deforming when advancing inside a body. In some embodiments, two sutures (16, 18) are captured by a suture threader (102) (FIG. 7*a*) and threaded into the plication lock delivery system (100); the two sutures (16, 18) extend from the distal end (22) of the lock assembly (20) and through the longitudinal lumen (26) of the lock assembly (20) and the catheter assembly (40), and exit from a suture port (62) on the control assembly (60). In some embodiments, the plication lock delivery system (100) is inserted into the body and tracked over the two sutures (16, 18) distally toward the pledgets (12, 14). In some embodiments, a tissue plication starts by engaging one suture to a suture tension mechanism (64) on the control assembly (60) and applying tension to the suture. Doing so can, for example, align the lock assembly (20) with the pledget where the suture extends from. In some embodiments, the second suture is engaged to the tissue plication mechanism (68). Upon applying tension to this second suture, the two pledgets (12, 14) can be pulled closer to each other. In some embodiments, while maintaining tension on the sutures (16, 18), the lock assembly (20) is deployed, thereby securing the sutures (16, 18) in a tensioned state. In some embodiments, the control assembly (60) is then used to release the lock assembly (20) from the catheter assembly (40), removing the plication lock delivery system (100) entirely from the body and leaving the lock assembly (20) to secure the tissue plication. In some embodiments, a suture cutter (not shown) can then be advanced to a proximity to the lock assembly (20) and be used to remove the excess suture. Both the suture cutter and the severed sutures can then be removed completely from the patient.

Figure 2A:
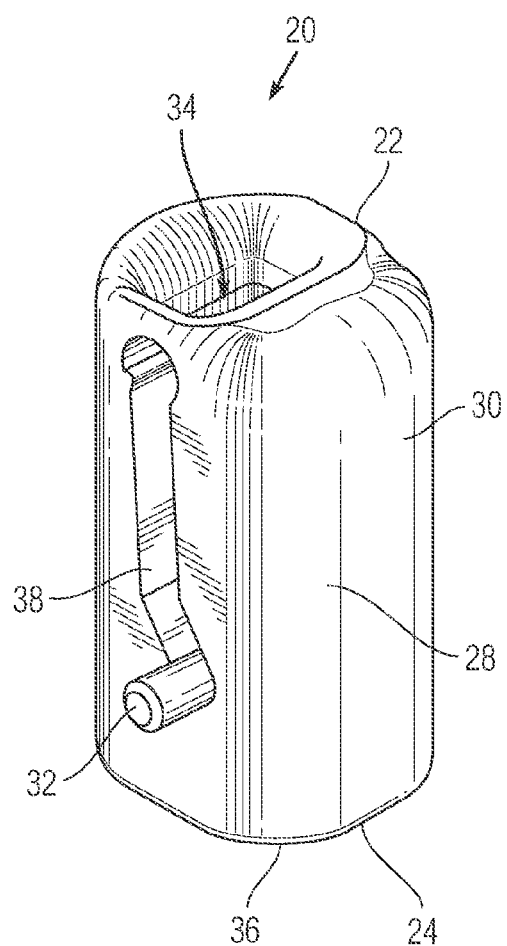
FIG. 2a is a perspective view of an exemplary lock assembly in accordance with the present teachings.
Figure 2B:
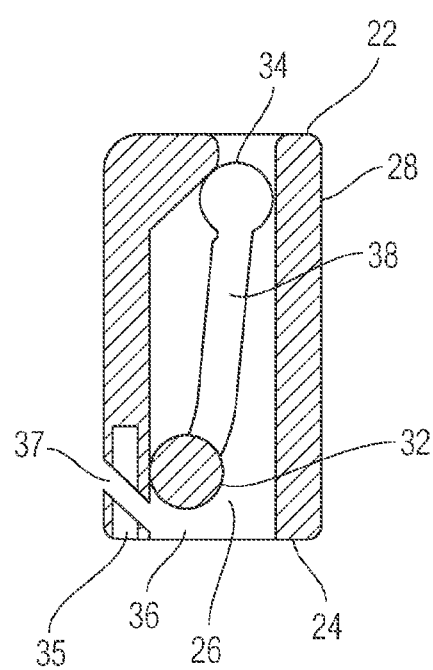
FIG. 2b is a perspective cross-section of an exemplary lock assembly in accordance with the present teachings.

FIGS. 2a-b illustrate the exemplary lock assembly (20) according to various embodiments of the present teachings. As illustrated in FIG. 2a, the exemplary lock assembly (20) includes a lock body (30) and a lock pin (32); the lock body (30) has an elongated body with a distal end (22), a proximal end (24) and a longitudinal lumen (26) extending from the distal end (22) to the proximal end (24) parallel to the longitudinal axis of the lock body (30), and the longitudinal lumen (26) includes a distal opening (34) and a proximal opening (36). In various embodiments of the present teachings, the longitudinal lumen (26) has a general width of about 1-3 mm and the lock body (30) has a general length of about 3-10 mm and a general outside diameter of about 2-5 mm. In some embodiments of the present teachings, the distal opening (34) is smaller than the proximal opening (36). In other embodiments of the present teachings, the distal opening (34) has a same size as the proximal opening (36). In yet other embodiments of the present teachings, the distal opening (34) is greater than the proximal opening (36). One skilled in the art should understand that the sizes of the openings (34, 36) at the distal and proximal ends (22, 24) of the lock body (30) vary according to the size, shape, material of the mitral valve annulus implant.

Continuously referring to FIG. 2a, the exemplary lock body (30) includes a tubular surface (28) and a slot (38) extending from one side of the tubular surface (28) to the opposite side of the tubular surface (28), intersecting the longitudinal lumen (26). As shown in FIG. 2a, the slot (38) is angled or curved against the longitudinal axis of the lock body (30) and extends from the distal end (22) to the proximal end (24). In some embodiments, the distal end of the slot is adjacent to the distal end (22) of the lock body (30). In some embodiments, the proximal end of the slot is adjacent to the proximal end (24) of the lock body (30). In certain embodiments, the slot (38) is configured to retain the lock pin (32).

As seen in FIG. 2a, the lock pin (32) is slidably disposed within the slot 38 on the exemplary lock body (30). In some embodiments, the lock pin (32) has a general elongated body with a center portion and two ends, each of which is narrower than the center portion (i.e., tapered ends). In certain embodiments, when the lock pin (32) is retained by the slot 38, the center portion is trapped inside the intersection formed by the slot (38) and the longitudinal lumen (26), and two narrower ends of the lock pin (32) extend laterally outside of the tubular surface (28) of the lock body (30). In particular embodiments, the lock pin (32) has a general length of 2-5 mm, with the center portion having a diameter of 0.5-2 mm and the ends each having a diameter of 0.25-1 mm.

According to various embodiments, without engaging sutures inside the lock assembly (20), the lock pin (32) slides freely from one end to the other end of the slot (38). In these embodiments, because the slot is curved or angled against the longitudinal axis of the lock body (30), as the lock pin (32) sliding from one end to the other end of the slot (38), the space between one side of the lock pin (32) to the inner lumen wall of the lock body (30) gradually changes. According to some embodiments of the present teachings, for example as illustrated in FIG. 8b, two sutures (16, 18) extend through the longitudinal lumen (26) of the lock body (30) and are positioned on one side of the lock pin (32). In certain embodiments, when the lock pin (32) is positioned at the proximal end of the slot (38), the space (39) where the sutures (16, 18) taken up between the lock pin (32) to the inner lumen wall of the lock body (30) is the greatest. In certain embodiments, when the lock is positioned at the distal end of the slot (38), the space (39) where the sutures (16, 18) taken up between the lock pin (32) to the inner lumen wall of the lock body (30) is the smallest. In certain embodiments, as the lock pin (32) slides from the proximal end to the distal end of the slot (38), the space (39) where the sutures (16, 18) taken up between the lock pin (32) and the inner lumen wall of the lock body (30) is reduced. In certain embodiments, as the lock pin (32) reaches a certain place in the slot (38), the sutures (16, 18) are compressed between the lock pin (32) and the lock body (30), which prevents the sutures (16, 18) from moving.

According to various embodiments of the present teachings, the cross section of a lock body (30) and/or a lock pin (32) may be circular or polygonal, such as square or hexagonal. Although the lock body (30) disclosed above is a single component in various embodiments, it should be understood by those skilled in the art that the lock body (30) device may be fabricated as a two-piece (or multi-piece) component and the two (or multiple) components are connected to form the entire lock assembly (20). For example, in order to assemble the lock pin (32) inside the lock body (30), the lock body (30) can have a top cap and a bottom body so that the cap and body can be joined together after the lock pin (32) is inserted. It should be understood by those skilled in the art that certain design features of the lock body (30) can be modified for ease of assembling with the lock pin (32). For example, the distal end of the slot (38) can have a larger side opening (37), allowing the center portion of the lock pin (32) to slide through.

In some embodiments of the present teachings, a lock body (30) can be fabricated by laser-cutting or acid-etching a pattern into a preformed tube. In other embodiments, a lock body (30) can be formed from a hollow tube that has been slotted, for example, by using a machining laser, EDM, or other methods, and then expanded to form an open structure.

Now referring to FIG. 2b, the exemplary lock body (30) can further include a side opening (37) extending from the tubular surface (28) of the lock body (30) to the longitudinal lumen (26) and a blind hole (35) extending from the proximal end (24) of the lock body (30) and intersecting and passing through and beyond the side opening (37). In various embodiments of the present teachings, the side opening (37) on the tubular surface is close to the proximal end (24) of the lock body (30). In some embodiments, the side opening (37) is perpendicular to the longitudinal axis of the lock body (30). In some embodiments, the side opening (37) is angled to the longitudinal axis of the lock body (30). In some embodiments, the blind hold (35) is parallel to the longitudinal axis of the lock body (30). In some embodiments, the blind hole (35) is not parallel to the longitudinal axis or the longitudinal lumen (26) of the lock body (30). In some embodiments of the present teachings, the distal end of the blind hole (35) is distal to its intersection to the side opening (37). The blind hole (35) can be configured to receive a post (43) on the distal end (42) of the inner catheter (46) as explained in detail herein. The side opening (37) can be configured to receive a pull wire (50) including a loop (52) thereof as described herein. In some embodiments of the present teachings, the side opening (37) has a general height of 0.25-1 mm and a length of 0.5-2 mm. In some embodiments, the blind hole (35) has a general diameter of 0.25-1 mm and a length of 1-3 mm.

In various embodiments of the present teachings, one or both of the lock body (30) and the lock pin (32) are made of a biocompatible metal, such as stainless steel, nitinol, Titanium, Elgiloy, Vitalium, Mobilium, Ticonium, Platinore, Stellite, Tantalum, Platium, Hastelloy, CoCrNi alloys (e.g., trade name Phynox), MP35N, or CoCrMo alloys or other metallic alloys. In other embodiments of the present teachings, one or both of the lock body (30) and the lock pin (32) are made of a biocompatible polymer, such as PTFE, UHMPE, HDPE, polypropylene, polysulfone, a mixture thereof, or other biocompatible plastic materials. In some embodiments where the lock body (30) and/or the lock pin (32) is made of a biocompatible polymer, a radioopaque marker is also used to assist visualization, for example, fluoroscopically. In other embodiments of the present teachings, the surface finish of the lock body (30) is textured to induce tissue response and tissue in-growth for improved stabilization.

Figure 3A:
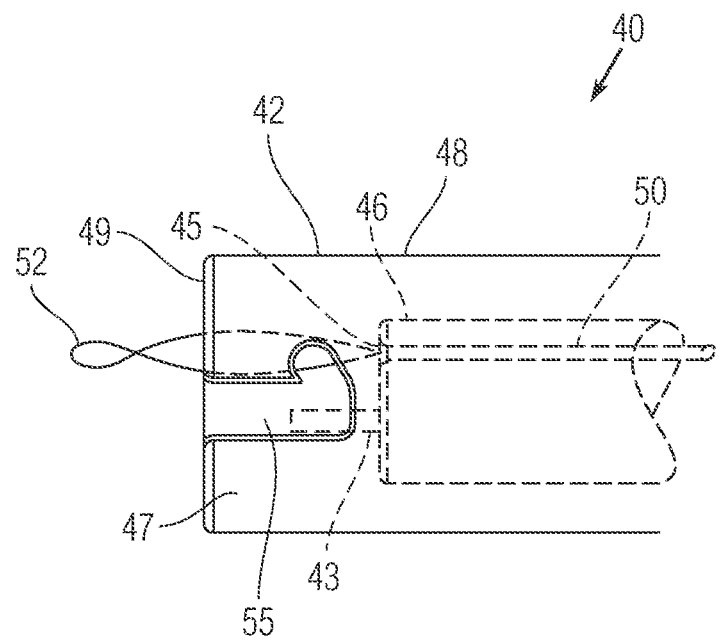
FIG. 3a is a sectional view of an exemplary catheter assembly in accordance with the present teachings.

FIG. 3a illustrates an embodiment of the distal end portion (42) of a catheter assembly (40) of the present teachings. In some embodiments, the catheter assembly (40) has a distal end portion (42) as illustrated and a proximal end portion (not shown) connecting to a control assembly (60). In some embodiments, the catheter assembly (40) includes an outer sheath (48), an inner catheter (46), and a pull wire (50). In some embodiments, the outer sheath (48) of the catheter assembly (40) has a proximal end (not shown) connecting to the control assembly (60), a distal end (49) configured to push a lock pin (32) distally, and an elongated lumen (47) extending along the longitudinal axis of the outer sheath (48) from the distal end (49) to the proximal end (not shown) As shown, the inner catheter (46) is located within the interior of the outer catheter (48) and does not extend distally beyond in this position. In some embodiments, the inner catheter (46) is slidably disposed within the elongated lumen (47) of the outer sheath (48). In some embodiments, the inner catheter (46) also has a distal end (45) configured to contact the proximal end (24) of the lock body (30), a proximal end (not shown) connecting to the control assembly (60), and at least one elongated lumen extending along the longitudinal axis of the inner catheter (46) from the distal end (45) to the proximal end (not shown). In some embodiments, the distal end (45) of the inner catheter (46) has a distal post (43) extending distally and is configured to slide inside the blind hole (35) on the lock body (30). In some embodiments, the pull wire (50) is slidably disposed within the inner catheter lumen. In some embodiments, the pull wire (50) includes a wire loop (52) at a distal end and is configured to extend through the side opening (37) on the lock body (30). In some embodiments, the pull wire (50) connects to a lock deploy-and-release mechanism (70) on the control assembly (60). According to some embodiments of the present teachings, the pull wire (50) is an elongated wire with a loop formed at its distal end. In other embodiments of the present teachings, the pull wire (50) is an elongated hypotube with the wire loop (52) disposed at a distal end of the hypotube.

In various embodiments of the present teachings, the pull wire (50) or the distal loop (52) of the pull wire (50) is constructed from a suture-like material. However, the construction or the materials should not be considered limiting and alternative embodiments include those described in details herein. According to some embodiments, the wire used to form the pull wire (50) or the distal loop (52) of the pull wire (50) has a general diameter from about 0.02 mm to about 1 mm. In some embodiments of the present teachings, the pull wire (50) is made of a biocompatible metal including stainless steel, nitinol, Titanium, Elgiloy, Vitalium, Mobilium, Ticonium, Platinore, Stellite, Tantalum, Platium, Hastelloy, CoCrNi alloys (e.g., trade name Phynox), MP35N, or CoCrMo alloys or other metallic alloys. In other embodiments, the pull wire (50) is made of a biocompatible polymer including PTFE, UHMPE, HDPE, polypropylene, polysulfone, and mixture thereof.

Figure 3B:
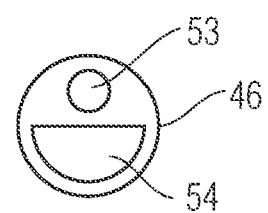
FIG. 3b is a cross-sectional view of an exemplary inner catheter in accordance with the present teachings.

In various embodiments of the present teachings, after sliding through the lock assembly (20), two sutures (16, 18) are inserted, extending from the distal end (45) of the inner catheter (46) proximally, exiting the proximal end (not shown) of the inner catheter (46), and reaching a suture port (62) on the control assembly (60). According to some embodiments of the present teachings, the inner catheter (46) includes an elongated lumen when both the pull wire (50) and sutures (16, 18) are slidably disposed within. In other embodiments of the present teachings, as a cross-section view illustrated in FIG. 3b, the inner catheter (46) includes two elongated lumens (53, 54) side by side, either parallel or unparallel to each other, where two sutures (16, 18) are slidably disposed within one lumen (54), and a pull wire (50) is slidably disposed within the other (53). Yet in other embodiments, the inner catheter (46) includes three elongated lumens side by side, either parallel or unparallel to one other, where each of the suture is slidably disposed within one lumen and a pull wire (50) is slidably disposed within the other. In yet other embodiments, the inner catheter (46) includes more than three elongated lumens.

According to various embodiments of the present teachings, the lock assembly (20) is configured to be slidably disposed within the distal end portion of the outer sheath (48) in part or in whole, and the outer sheath (48) is configured to push on the two narrow ends of the lock pin (32) extending outside of tubular surface of the lock body (30). As shown in FIG. 3a, in an exemplary embodiment, the distal end (49) of the outer sheath (48) also includes at least one slot (55) each extending from the distal end (49) of the outer sheath (48) proximally and the slots are disposed across one other and extend along the longitudinal axis of the outer sheath (48). The slots (55) are thus formed along an inner surface of the outer sheath (48). In some embodiments, the slot (55) on the outer sheath (48) match the slot (38) on the lock body (30) so that as the lock assembly (20) slides within the elongated lumen (47) of the outer sheath (48), the narrow ends of the lock pin (32) slide within the slot (55) on the outer sheath (48). In some embodiments when the outer sheath (48) extends distally relative to the lock assembly (20), the lock pin (32) is pushed distally by the distal end (49) of the outer sheath (48) and slides along the slot (38) on the lock body (30) distally. Alternatively, in some embodiments where the lock assembly (20) is pulled proximally relative to the outer sheath (48), the lock pin (32) is pushed distally by the distal end (49) of the outer sheath (48) along the slot (38) on the lock body (30). One skilled in the art would appreciate that other design configurations could also be incorporated to achieve the same function or obvious variations thereof. For example, the outer sheath (48) can have a flat distal end (49).

In various embodiments of the present teachings, the outer sheath (48) and the inner catheter (46) can be formed from a variety of materials. Typical materials used to construct the catheters and/or the sheaths of the present teachings can comprise commonly known materials such as Amorphous Commodity Thermoplastics that include Polymethyl Methacrylate (PMMA or Acrylic), Polystyrene (PS), Acrylonitrile Butadiene Styrene (ABS), Polyvinyl Chloride (PVC), Modified Polyethylene Terephthalate Glycol (PETG), Cellulose Acetate Butyrate (CAB); Semi-Crystalline Commodity Plastics that include Polyethylene (PE), High Density Polyethylene (HDPE), Low Density Polyethylene (LDPE or LLDPE), Polypropylene (PP), Polymethylpentene (PMP); Amorphous Engineering Thermoplastics that include Polycarbonate (PC), Polyphenylene Oxide (PPO), Modified Polyphenylene Oxide (Mod PPO), Polyphenelyne Ether (PPE), Modified Polyphenelyne Ether (Mod PPE), Polyurethane (PU), Thermoplastic Polyurethane (TPU); Semi-Crystalline Engineering Thermoplastics that include Polyamide (PA or Nylon), Polyoxymethylene (POM or Acetal), Polyethylene Terephthalate (PET, Thermoplastic Polyester), Polybutylene Terephthalate (PBT, Thermoplastic Polyester), Ultra High Molecular Weight Polyethylene (UHMW-PE); High Performance Thermoplastics that include Polyimide (PI, Imidized Plastic), Polyamide Imide (PAI, Imidized Plastic), Polybenzimidazole (PBI, Imidized Plastic); Amorphous High Performance Thermoplastics that include Polysulfone (PSU), Polyetherimide (PEI), Polyether Sulfone (PES), Polyaryl Sulfone (PAS); Semi-Crystalline High Performance Thermoplastics that include Polyphenylene Sulfide (PPS), Polyetheretherketone (PEEK); and Semi-Crystalline High Performance Thermoplastics, Fluoropolymers that include Fluorinated Ethylene Propylene (FEP), Ethylene Chlorotrifluroethylene (ECTFE), Ethylene, Ethylene Tetrafluoroethylene (ETFE), Polychlortrifluoroethylene (PCTFE), Polytetrafluoroethylene (PTFE), Expanded Polytetrafluoroethylene (ePTFE), Polyvinylidene Fluoride (PVDF), Perfluoroalkoxy (PFA). Other commonly known medical grade materials that can be used in embodiments of the present teachings include elastomeric organosilicon polymers, polyether block amide or thermoplastic copolyether (PEBAX), Kevlar, and metals such as stainless steel and nickel/titanium (nitinol) alloys. In other embodiments, the outer sheath (48) and inner catheter (46) includes at least one radioopaque marker element. In some embodiments, the radioopaque marker is near the distal end of the outer sheath (48) and the inner catheter (46). In some embodiments, the radioopaque marker elements are made of a metal or a metal alloy, such as, for example, one or more of nitinol, Elgiloy®, Phynox®, MP35N, stainless steel, nickel, titanium, gold, rhenium, tungsten, palladium, rhodium, tantalum, silver, ruthenium, hafnium, and alloys thereof.

In various embodiments, the outer sheath (48) and inner catheter (46) have a general diameter of 2.5-5 mm and 2-4.5 mm respectively.

Figure 4A:
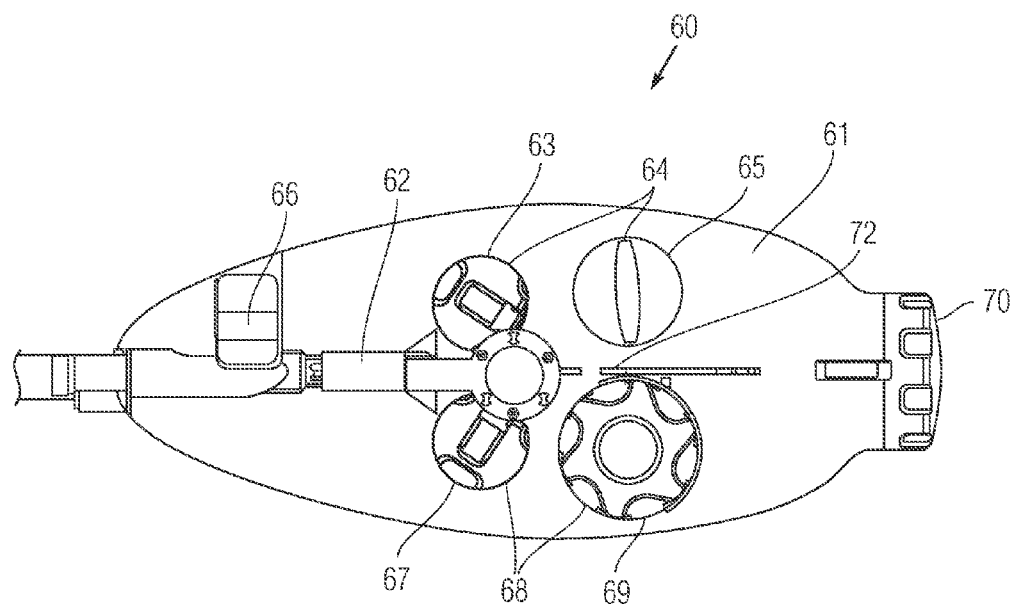
FIGS. 4a and 4b are top plan views of an exemplary control assembly of a plication lock delivery system in accordance with the present teachings.
Figure 4B:
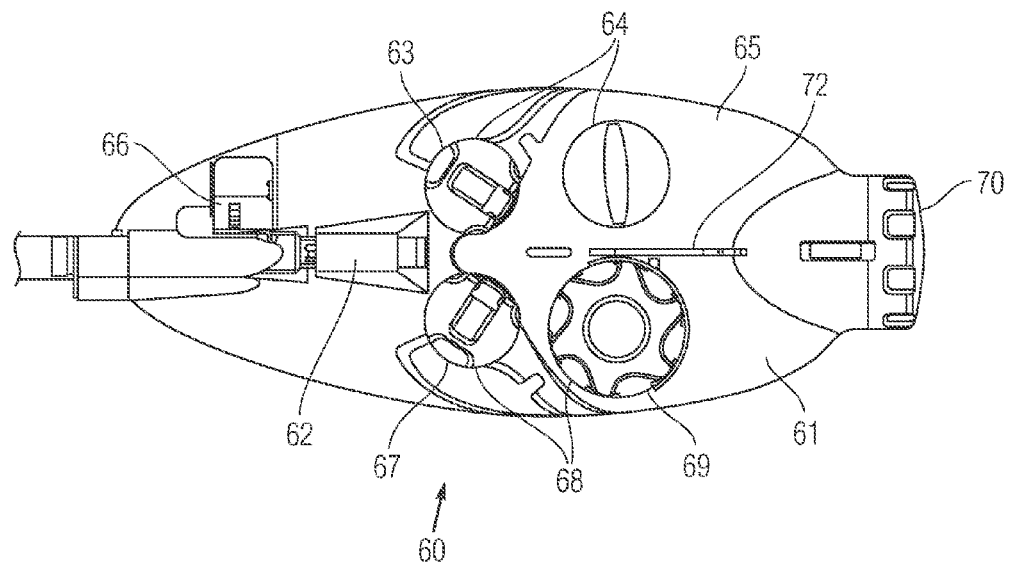

FIGS. 4a and 4b illustrate an exemplary control assembly (60). In various embodiments, the control assembly (60) has a housing (61), holding various control mechanisms, and a suture port (62) on the control assembly (60), allowing a suture threader (102) and sutures (16, 18) extending in and out of a plication lock delivery system (100). In various embodiments, a first suture clamp (63) secures one suture, while allowing the suture tension mechanism (64) to apply tension to the suture. In various embodiments, a second suture clamp (67) secures the other suture, while allowing the tissue plication mechanism (68) to apply tension to the suture and plicate the tissue. In some embodiments, a lock deploy-and-release mechanism (70) deploys the lock assembly (20) to secure tissue plication and releases the lock assembly (20). In some embodiments of the present teachings, the lock deploy-and-release mechanism (70) also includes an indicator (72) to guide a clinician during the lock assembly (20) deployment and releasing steps. In certain embodiments, as illustrated in FIG. 4, an exemplary control assembly (60) also includes a pre-load cam (66) as described herein.

Figure 5A:
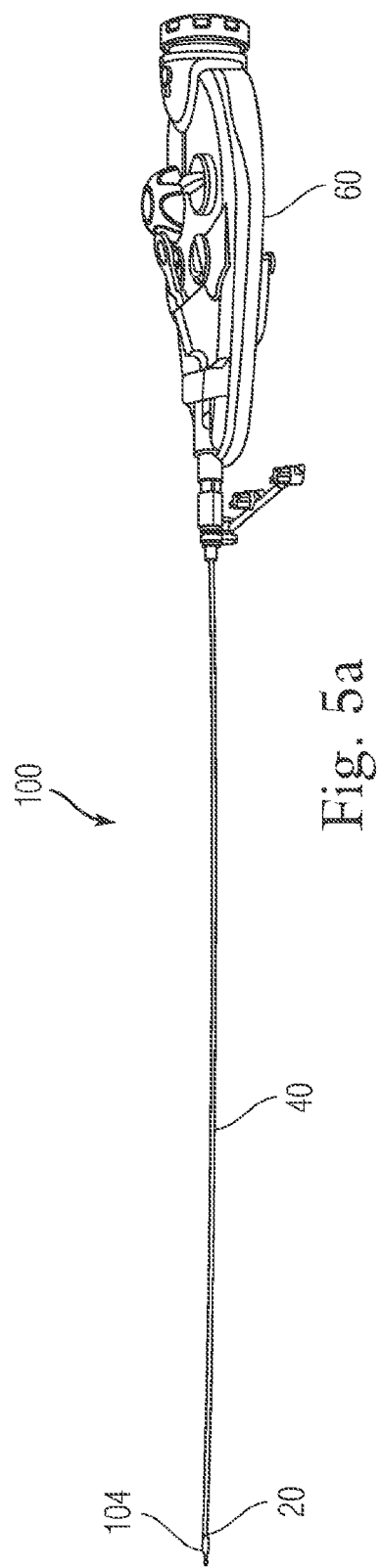
FIG. 5a is a side perspective view of an exemplary plication lock delivery system in accordance with the present teachings.
Figure 5B:
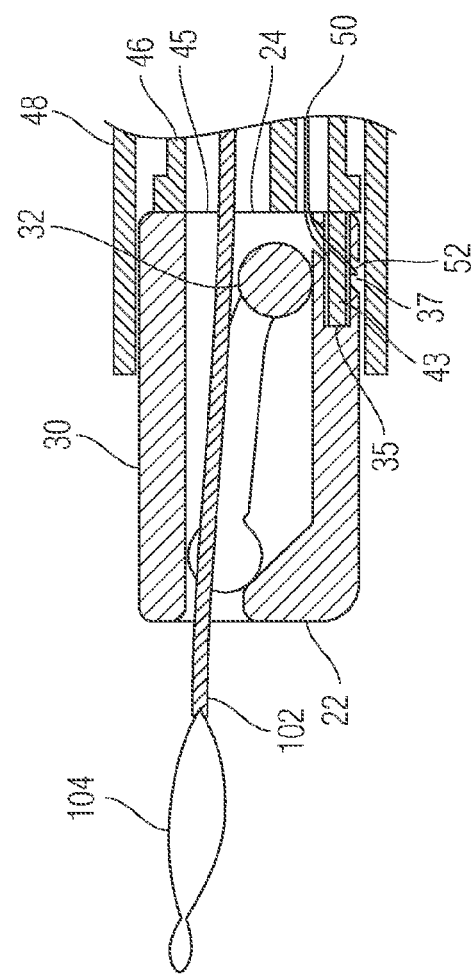
FIG. 5b is a cross-sectional view of an exemplary plication lock delivery system in accordance with the present teachings.

FIG. 5a illustrates an exemplary plication lock delivery system (100) of the present teachings, where a lock assembly (20), a catheter assembly (40) and a control assembly (60) are assembled in accordance with various embodiments of the present teachings. As shown in FIG. 5b (a cross-section view of the distal end portion of the plication lock delivery system (100) with a suture threader disposed within), the distal loop (52) of a pull wire (50) extends across a side opening (37) on the exemplary lock assembly (20), and a distal post (43) on an inner catheter (46) of the exemplary catheter assembly (40) slides across the distal loop of the pull wire (50) and enters a blind hole (35) on the lock body (30). In some embodiments, upon pulling the pull wire (50) proximally, the lock assembly (20) and the inner catheter (46) are joined together with the distal end (45) of the inner catheter (46) contacting the proximal end (24) of the lock body (30); the outer sheath (48) slides over the lock assembly (20) and inner catheter (46), and the distal end portion of the outer sheath (48) covers the distal end (45) of the inner catheter (46) and at least some proximal portion of the lock assembly (20). In certain embodiments, the catheter assembly (40) is further joined to the control assembly (60), for example, the pull wire (50) joined to the lock deploy-and-release mechanism (70) on the control assembly (60).

Figure 6A:
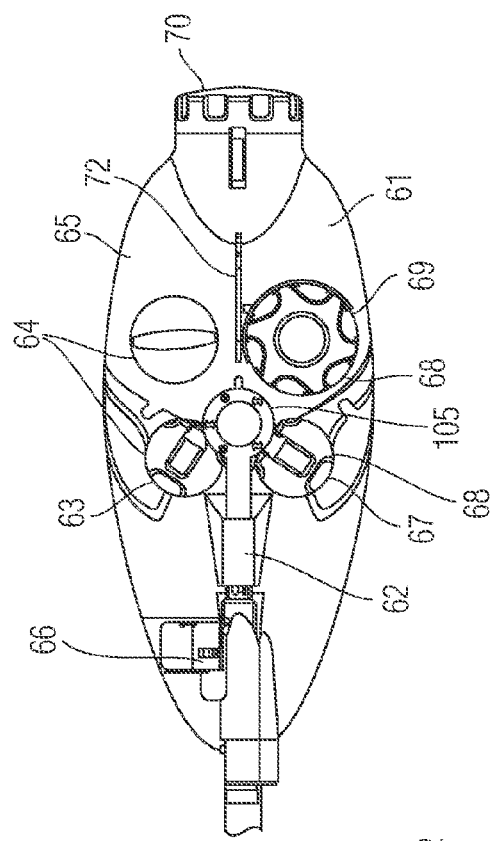
FIG. 6a is a top plan view of an exemplary control assembly of a plication lock delivery system in accordance with the present teachings.
Figure 6B:
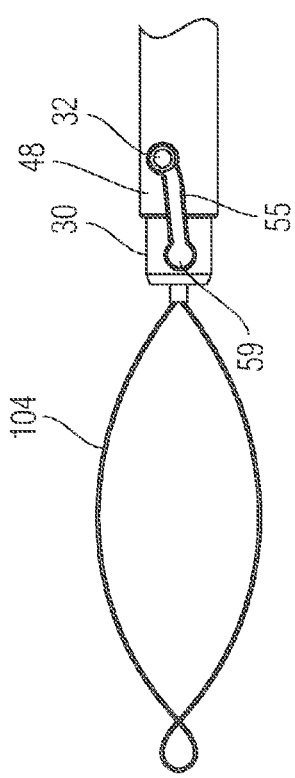
FIG. 6b is a side elevation view of an exemplary plication lock delivery system in accordance with the present teachings.

FIGS. 6a-b illustrate an exemplary embodiment of the present teachings where a plication lock delivery system (100) is set to deliver a suture lock assembly (20). In some embodiments of the present teachings, in order to prevent movement of the lock pin (32) and lock body (30) relative to the inner catheter (46) as the plication lock delivery system tracks through tortuous paths inside a body, the plication lock delivery system (100) is put in a pre-load configuration during a percutaneous delivery. In such a pre-load configuration, an outer sheath (48) with lock pin (32) engaged at its tip is configured to resist distal push by the inner catheter (46). One skilled in the art should understand that mechanisms other than what is described in details herein can be incorporated to achieve this purpose. What has been disclosed below is merely exemplary non-limiting embodiments.

FIG. 6b illustrates an exemplary embodiment of the pre-load configuration where a lock pin (32) is retained at the proximal end of a slot (38) on a lock body (30) of the present teachings during a percutaneous advancement. In one exemplary embodiment of the present teachings, the distal end portion of an outer sheath (48) can be incorporated in a "J-shaped" slot (55), so that a distal push by the inner catheter (46) will trap the lock pin (32) inside the upward tip (59) of the slot (55). In this embodiment, the outer sheath (48) provides a proximal resistance to the inner catheter (46), preventing the inner catheter (46) from deforming longitudinally. As the exemplary plication lock delivery system (100) tracks around curves inside the body, when the inner catheter (46) starts to deform longitudinally with the lock pin (32) trapped inside the J slot (55), the outer sheath (48) resists the distal push of the inner catheter (46). Although not shown in FIG. 6b, during such an exemplary advancement, the pull wire (50) is pulled proximally in order to maintain the contact between the inner catheter (46) and the lock assembly (20). In an exemplary embodiment of the present teachings where a tissue plication lock delivery system (100) is in the pre-load configuration, the inner catheter (46) is compressed by the outer sheath (48), the outer sheath (48) is in tension by the inner catheter (46). In some embodiments, as shown in FIG. 6a, a pre-load cam (66) can be activated on the control assembly (60) of the plication lock delivery system (100) in order to switch the plication lock delivery system (100) from other configurations to the pre-load configuration and provide ease of use to a clinician. In other embodiments of the present teachings, other mechanisms can be incorporated to achieve the pre-load configuration. In yet other embodiments, a pre-load configuration is not required for tissue plication.

Figure 7A:
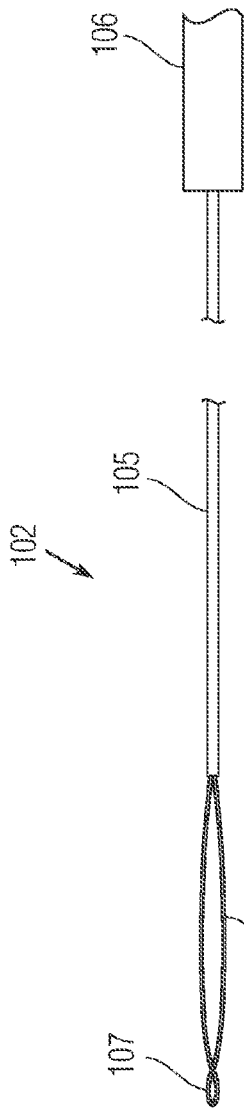
FIG. 7a is a side elevation view, in partial breakaway, of a suture threader in accordance with the present teachings.

In various embodiments, before advancing a plication lock delivery system (100) of the present teachings inside a body, a suture threader (102) is loaded inside the plication lock delivery system (100) to capture sutures. As shown in FIG. 7a, the suture threader (102) has a distal loop (104) for sutures to slide through, an elongated body (105), and a proximal tab (106) for ease of handling by a clinician. In some embodiments, a clinician loads sutures threader (102) to the plication lock delivery system (100) by inserting a suture threader (102) inside the suture port (62) on the control assembly (60), extending suture threader (102) distally through the suture lumen in the inner catheter (46), continue distally through the lumen (26) of the lock assembly (20), with the distal loop (104) of the suture threader (102) coming out of the distal end (22) of the lock assembly (20), and the proximal tab (106) of the suture threader (102) remains partially inserted inside suture port, as illustrated in FIGS. 6a-b. In other embodiment, the plication lock delivery system (100) is pre-packaged with suture threader (102) already loaded. A clinician then load sutures (16, 18) to the plication lock delivery system (100) by first inserting the sutures (16, 18) through the distal loop (104) of the suture threader (102) as illustrated in FIG. 7b, then pulling the suture threader tab (106) proximally allowing the suture threader (104) sliding distally through the suture lumen of the inner catheter (46) carrying sutures (16, 18). In some embodiments, as the suture threader (102) is pulled proximally, the sutures (16, 18) enter the distal end (22) of the lock assembly (20), travel through the lock body lumen (26), exit at the proximal end (24) of the lock body (30), enter the distal end (45) of the inner catheter (46), travel along the suture lumen of the inner catheter (46), exit at the proximal end of the suture lumen, reach the control assembly (60) at the proximal end of the inner catheter (46), and exit at the suture port (62) on the control assemble (60). Upon completion of such a suture threading, as illustrated in FIG. 8a, two proximal end portions of the sutures come out of the suture port (62) on the control assembly (60). FIG. 8b illustrates the lock assembly (20) and distal end portion of the catheter assembly (40) where two sutures (16, 18) are loaded inside and extend through the distal opening of the lock (20).

Referring back to FIG. 7a, in one exemplary embodiment, the distal loop (104) of the suture threader (102) includes a twist resulting general a "8"-shaped loop, with a smaller loop (107) at the distal end of the loop (104). This configuration, for example, allows the suture threader (102) to secure the sutures (16, 18) during threading and/or pulling. For example, when the suture threader (102) is pulled proximally, the sutures (16, 18) are pushed into the smaller distal loop (107) to prevent them from coming loose. In one embodiment, the twist ranges from 90°-360°.

In various embodiments, if one or both sutures is lost during the initial threading, the suture threader (102) can be reloaded into the plication lock delivery system (100) to repeat the threading step. In some embodiments, without activating the pre-load cam (66) on the control assembly, a suture threader (102) is prevented from being pulling proximally. In other embodiments, the plication lock delivery system (100) is pre-packaged with the suture threader (102) pre-loaded and the pre-load cam deactivated. In yet other embodiments of the present teachings, a suture threader is operated independently from the pre-load cam mechanism.

In various embodiments, a complete assembly, including a plication lock delivery system (100) and sutures (16, 18) loaded inside, is advanced to the treatment location by sliding inside a guide catheter placed inside a delivery track inside the body. In other embodiments of the present teachings, the system is advanced to a treatment location by tracking over the sutures (16, 18) enclosed within including a plication lock delivery system (100).

Figure 9A:
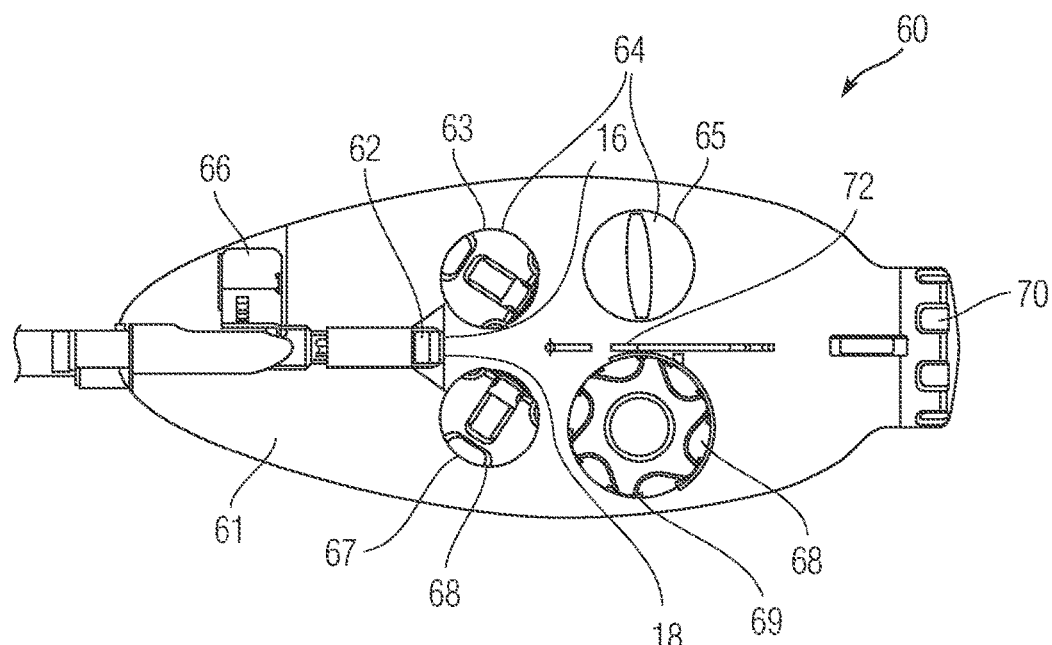
FIG. 9a is a top plan view of an exemplary control assembly of a plication lock delivery system in accordance with the present teachings.
Figure 9B:
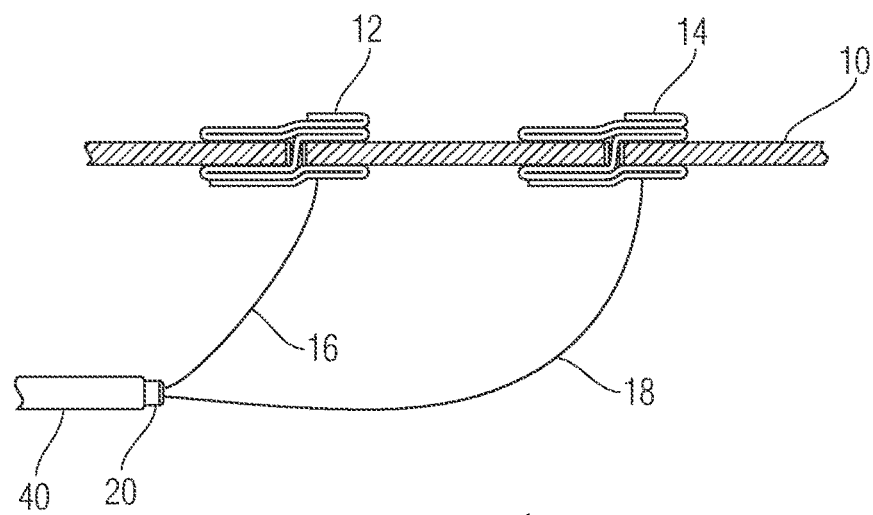
FIG. 9b is a partial cross-sectional view of two exemplary pledgets deployed at a mitral valve annulus, and an exemplary plication lock delivery system in accordance with the present teachings.

FIG. 9b illustrates an embodiment of the present teachings where the distal end portion of an exemplary assembly reaches the mitral valve annulus (10) and two pledgets (12, 14) have been implanted. Satisfied with the location, a clinician can now apply tension to the sutures (16, 18). Referring to FIG. 9a, a suture is shown to be loaded into an exemplary suture tension mechanism (64). According to various embodiments of the present teachings, the suture tension mechanism (64) includes a first suture clamp (63) and a tension means (65). In some embodiments, upon securing a first suture to the first suture clamp (63), a clinician activates the suture tension means (65) to apply tension to the first suture (e.g., by rotating a knob or the like). In some embodiments of the present teachings, a clinician aligns the lock assembly (20) to a pledget by applying tension to a suture extending from this pledget. In other embodiments, a clinician aligns the lock assembly (20) to one pledget by applying tension to a suture extending from the other pledget. In other embodiments, a clinician aligns the lock assembly (20) between the pledgets by applying tension to either of the two sutures (16, 18) extending from the two pledgets. In other embodiments of the present teachings, a first clutch mechanism (not shown) is incorporated in the control assembly (60) of the plication lock delivery system (100) so that as the tension on the suture reaches a certain level, such as 0.75 lb, the clutch mechanism (100) is activated to prevent the suture from being stretched beyond its limit. It should be understood by those skilled in the art that although a clamp (63) and a knob means (65) is shown in FIG. 9a, other designs can also be used here.

Figure 9C:
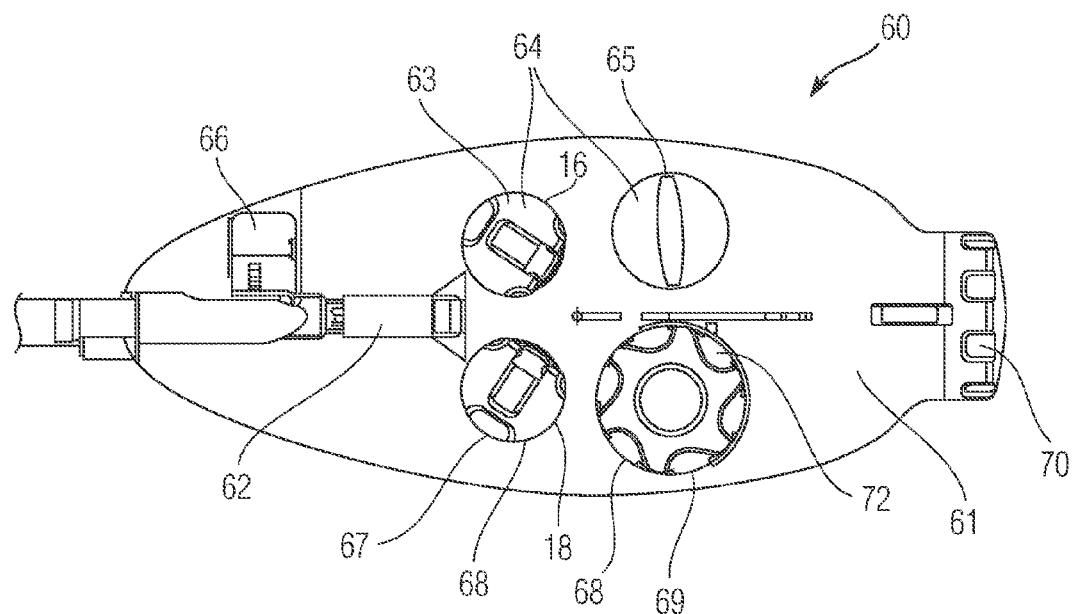
FIG. 9c is a top plan view of an exemplary control assembly of a plication lock delivery system in accordance with the present teachings.
Figure 9D:
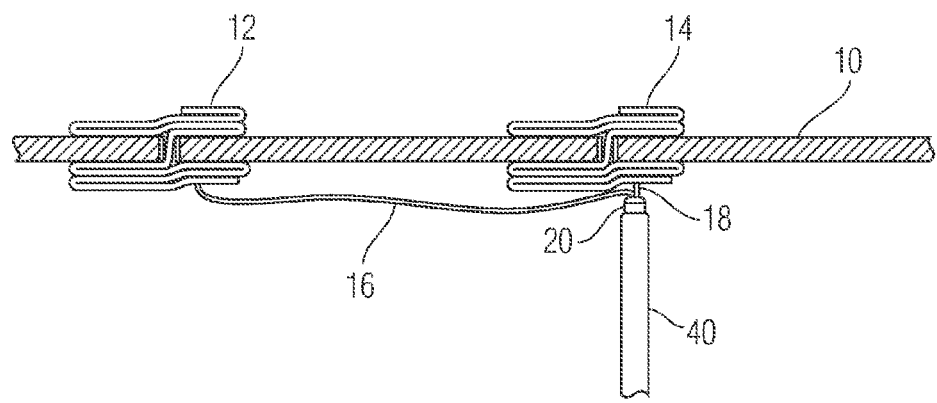
FIG. 9d is a cross-sectional view of an exemplary tissue plication and an exemplary plication lock delivery system in accordance with the present teachings.

Now referring to FIG. 9c, in various embodiments, while maintaining the tension on the first suture, a second suture is loaded into a tissue plication mechanism (68) and tension is applied to the second suture to plicate tissues. Similarly, according to some embodiments of the present teachings, the tissue plication mechanism (68) includes a second suture clamp (67) and a tissue plication means (69). In some embodiments, upon securing the second suture to the second suture clamp (67), a clinician activates the tissue plication means (69) which applies tension to the second suture. FIG. 9d illustrates tissues being plicated according to one embodiment of the present teachings. In some embodiments of the present teachings, a second clutch mechanism (not shown) is incorporated in the control assembly (60) so that as the tension on the second suture reaches a certain level, such as 5 lb, the clutch is activated to prevent the second suture from being stretched beyond its limit. In other embodiments, the degree of the tension applied to the suture can be determined by visualizing the amount of plication applied to the tissue, for example, fluoroscopically. Additionally, it should be understood by those skilled in the art that although a clamp and a knob means is shown in the drawing, other design can also be used.

In various embodiments of the present teachings, while the tissue plication mechanism (68) tensions the second suture, the first suture is prevented from coming loose by further activating the suture tension mechanism (64). In some embodiments, tension applied on one or both sutures can be released, for example, by activating a release button. In some embodiments, one or both sutures can be re-tensioned again.

In various embodiments of the present teachings, tension is applied to one or both sutures by spooling around a suture clamp (63, 67) which is coupled to an actuator, such as a knob, that can be manipulated by the user. In other embodiments of the present teachings, tension is applied to one or both sutures by linearly pulling on a suture clamp (63, 67) or drawing tension on sutures engaged between pinch rollers. Other mechanisms can also be used to apply tension to the suture.

Figure 10A:
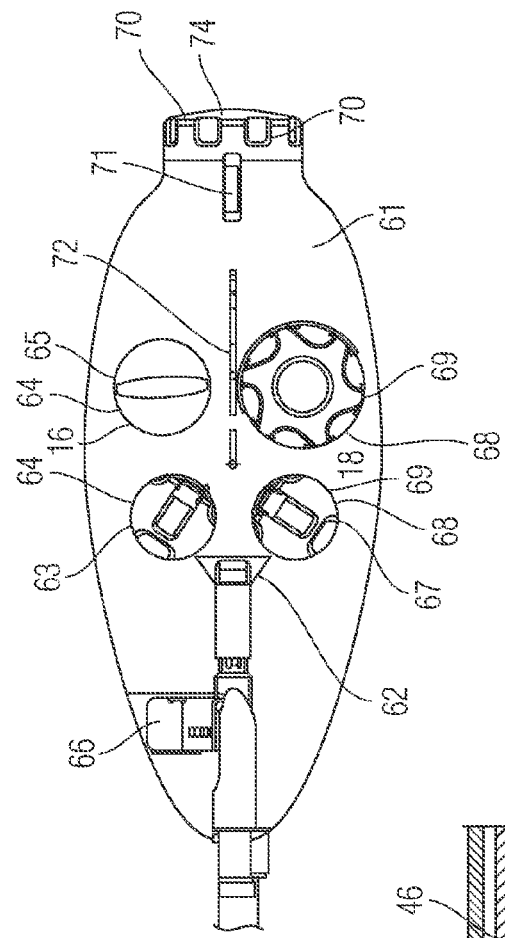
FIG. 10a is a top plan view of an exemplary control assembly of a plication lock delivery system in accordance with the present teachings.

In various embodiments, after a clinician is satisfied with the extent of the tissue plication, the lock assembly (20) is deployed. FIGS. 10a-b illustrate an embodiment of the lock deployment of the present teachings. In this embodiment, the lock deploy-and-release mechanism (70) includes a lockout button (71), an indicator (72), and a deploy-and-release means (74). The lockout button (71) can be used to prevent an accidental activation of the lock deploy-and-release mechanism (70). In some embodiments of the present teachings, without setting off such a lockout button (71), a clinician is prevented from activating the deploy-and-release means (74). The indicator (72) can provide a visual aid for the lock deployment and releasing process. Additionally, it should be understood by those skilled in the art that although a button design for the lockout (71), a fin design for the indicator (72), and a knob design for deploy-and-release means (74) is shown in the drawing, other designs and configurations of the lock deployment and release mechanism (70) can also be used. In some embodiments, a lockout function is eliminated or combined with the deploy-and-release means (74). In other embodiments, one or both of the lock out and indicator are not included in the lock deploy-and-release mechanism (70).

In various embodiments, to deploy the lock assembly (20), a clinician first initiates the lockout button (71) and activates the deploy-and-release means (74). In some embodiments, the lock deploy-and-release mechanism (70) pulls the pull wire (50) proximally relative to the outer sheath (48), which in turn pulls the lock body (30) proximally relative to the outer sheath (48). In certain embodiment, the lock pin (32) is pushed distally by the distal end of the outer sheath (48) to secure the sutures (16, 18) inside the lock assembly (20). In other embodiments, the lock deploy-and-release mechanism (70) pushes the outer sheath (48) distally while maintaining the pull wire (50) and the lock pin (32) is then pushed distally by the distal end of the outer sheath (48) to secure the sutures (16, 18) inside the lock assembly (20). In yet other embodiments of the present teachings, the lock deploy-and-release mechanism (70) pulls the pull wire (50) proximally and pushes the outer sheath (48) distally at the same time and the lock pin (32) is then pushed distally by the distal end of the outer sheath (48) to secure the sutures (16, 18) inside the lock assembly (20). FIG. 10b illustrates an embodiment of the present teachings, where sutures (16, 18) are secured by and located inside the lock assembly (20). As illustrated in FIG. 10b, during an exemplary lock deployment, the pull wire (50) remains threaded through a side opening (37) of the lock assembly (20) and is prevented from coming loose by the distal post (43) on the inner catheter (46).

In various embodiments of the present teachings, as illustrated in FIG. 10a, the indicator (72) of the lock deploy-and-release mechanism (70) moves from its first state to a second state, indicating the completion of a lock assembly (20) deployment.

Figure 10C:
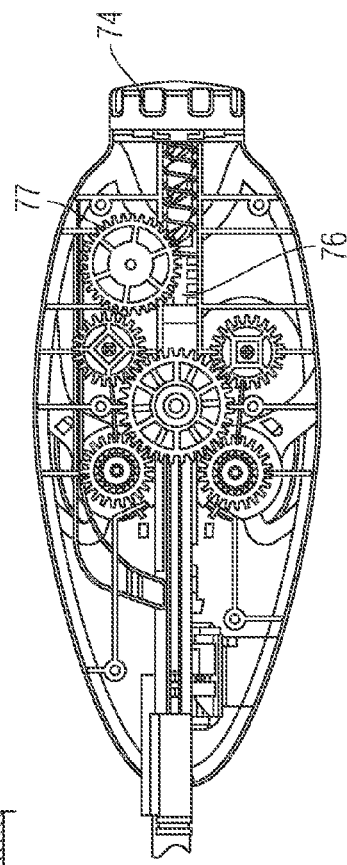
FIG. 10c is a top plan view, in partial breakaway, of an exemplary control assembly of a plication lock delivery system in accordance with the present teachings.
Figure 10B:
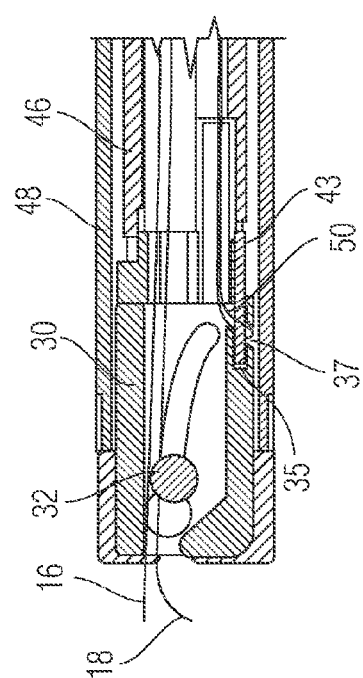
FIG. 10b is a cross-sectional view of an exemplary plication lock delivery system in accordance with the present teachings.

In various embodiments of the present teachings, as shown in FIG. 10c, a drive rack (76) is connected with the lock deploy-and-release means (74), the pull wire (50), and an outer sheath (48). In some embodiments, upon activating the deploy-and-release means (74), the drive-rack (76) is pulled proximally, which pulls the pull wire (50) proximally without affecting outer sheath (48). In other embodiments of the present teachings, a drive gear (77) is connected to the drive-rack (76) such that, upon activating the deploy-and-release means (74), the drive gear (77) causes a distal motion to the outer sheath (48) without affecting the pull wire (50). In other embodiments of the present teachings, upon activating the deploy-and-release means (74), the drive-rack (76) is pulled proximally, which pulls the pull wire (50) proximally and pushes the outer sheath (48) distally at the same time. Although an exemplary drive-rack (76) and an exemplary drive gear (77) are disclosed here, one skilled in the art should appreciate that other mechanisms can be incorporated to achieve the same functions and obvious variations thereof. In one embodiment, the lock assembly deployment is an automatic process, such that activating a spring can complete the travel of a drive rack.

In various embodiments, the deployment of a lock assembly (20) of the present teachings is measured by the travel distance of the pull wire (50) and outer sheath (48). In some embodiments, the travel distance is about 10-30 mm. In other embodiments, the deployment of a lock assembly (20) can be measured by the counter force received by the deploy-and-release means (74). For example, the distal travel by the lock pin (32) generates a greater counter force to the control assembly (60) as the sutures (16, 18) being compressed than before the sutures (16, 18) being compressed. In yet other embodiments, the deployment of the lock assembly (20) is monitored by changes in an indicator (72) on the control assembly (60).

In various embodiments, after sutures (16, 18) are secured by a lock assembly (20), the lock deploy-and-release means (74) stops the motion of the pull wire (50) and/or outer sheath (48), so that the pull wire (50) no longer restricts the distal movement of the lock body (30), and/or the outer sheath (48) no longer restricts the proximal movement of the lock pin (32). In various embodiments, at this time, the tension applied in the control assembly (60) on both sutures can be released, either with the sutures remaining inside the suture clamps (63, 67) or with the sutures (16, 18) released from the suture clamps (63, 67). In various other embodiments of the present teachings, the tension on the sutures (16, 18) is released automatically at the end of the lock assembly (20) deployment. At this time, a clinician can assess the lock deployment before the final release. In some embodiments, the indicator of the deployment release mechanism indicates the completion of a lock deployment step.

Figure 11A:
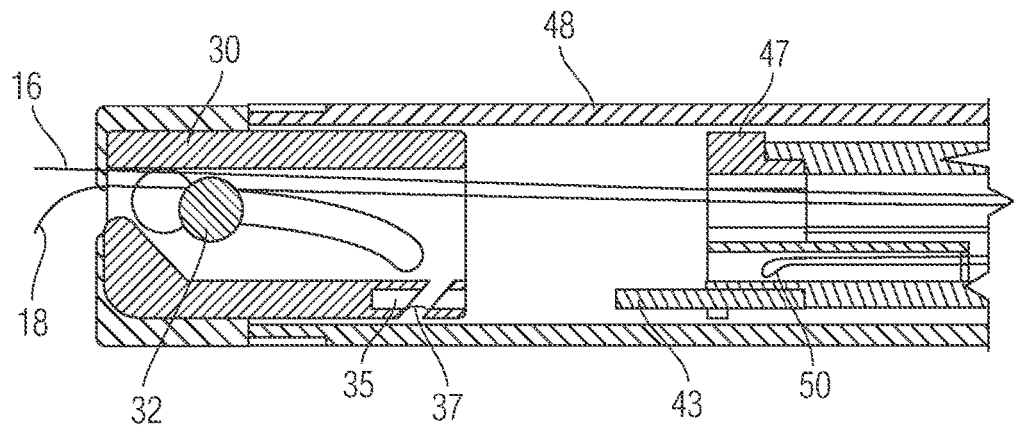
FIG. 11a is a cross-sectional view of an exemplary plication lock delivery system in accordance with the present teachings.

To release the lock assembly (20), in various embodiments, the deploy-and-release mechanism (70) is further activated, for example, by continuously activating the deploy-and-release means (74). In various embodiments, the deploy-and-release means (74) pulls the inner catheter (46) proximally relative to the pull wire (50), releasing the distal post (43) of the inner catheter (46) from the blind hole (35) of the lock body (30) and the distal loop (52) of the pull wire (50), freeing the pull wire (50) from the side opening (37) of the lock body (30). At this point in these embodiments, the lock assembly (20) is disconnected from the inner catheter (46) and the catheter assembly (40). In some embodiments, to remove the catheter assembly (40) from the body, two sutures (16, 18) are first released from the two suture clamps (63, 67) if a clinician has not already done so and the plication lock delivery system (100) is retracted out of the body, leaving behind the lock assembly (20) clamping on two sutures (16, 18). FIG. 11a illustrates an embodiment of the present teachings where the lock assembly (20) is released from the inner catheter (46) and catheter assembly (40).

Figure 11B:
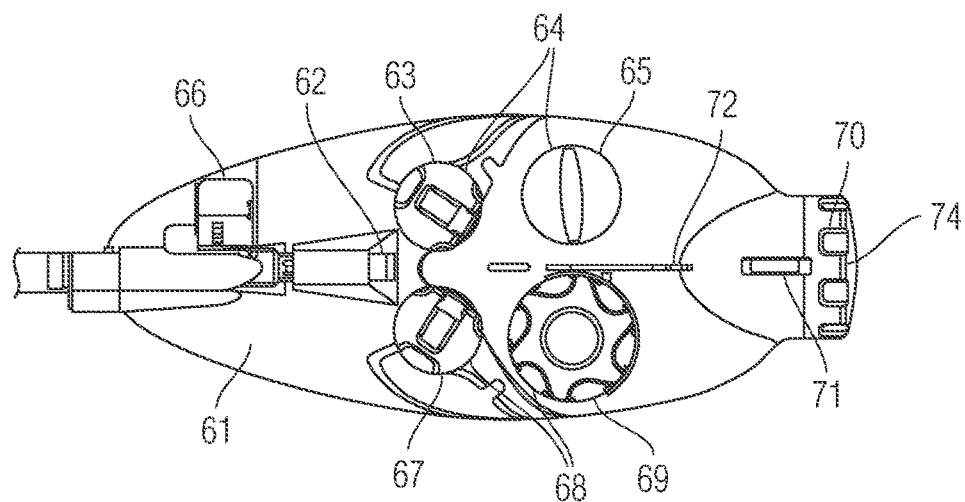
FIG. 11b is a top plan view of an exemplary control assembly of a plication lock delivery system in accordance with the present teachings.

In various embodiments of the present teachings, as illustrated in FIG. 11b, the indicator (72) of the lock deploy-and-release mechanism (70) moves from its second state to a third state indicating the completion of a lock assembly (20) releasement.

To further remove excess sutures in some embodiments, a suture cutter is advanced proximally to the lock and cuts the sutures. Both the suture cutter and the excess sutures can then be removed. One skilled in the art should understand that a variety of suture cutter designs can be used to remove the excess sutures. In addition, U.S. patent application Ser. No. 11/935,054, entitled "Suture cutter and method of cutting suture," filed Nov. 5, 2007, is incorporated herein by reference in its entirety.

Figure 12:
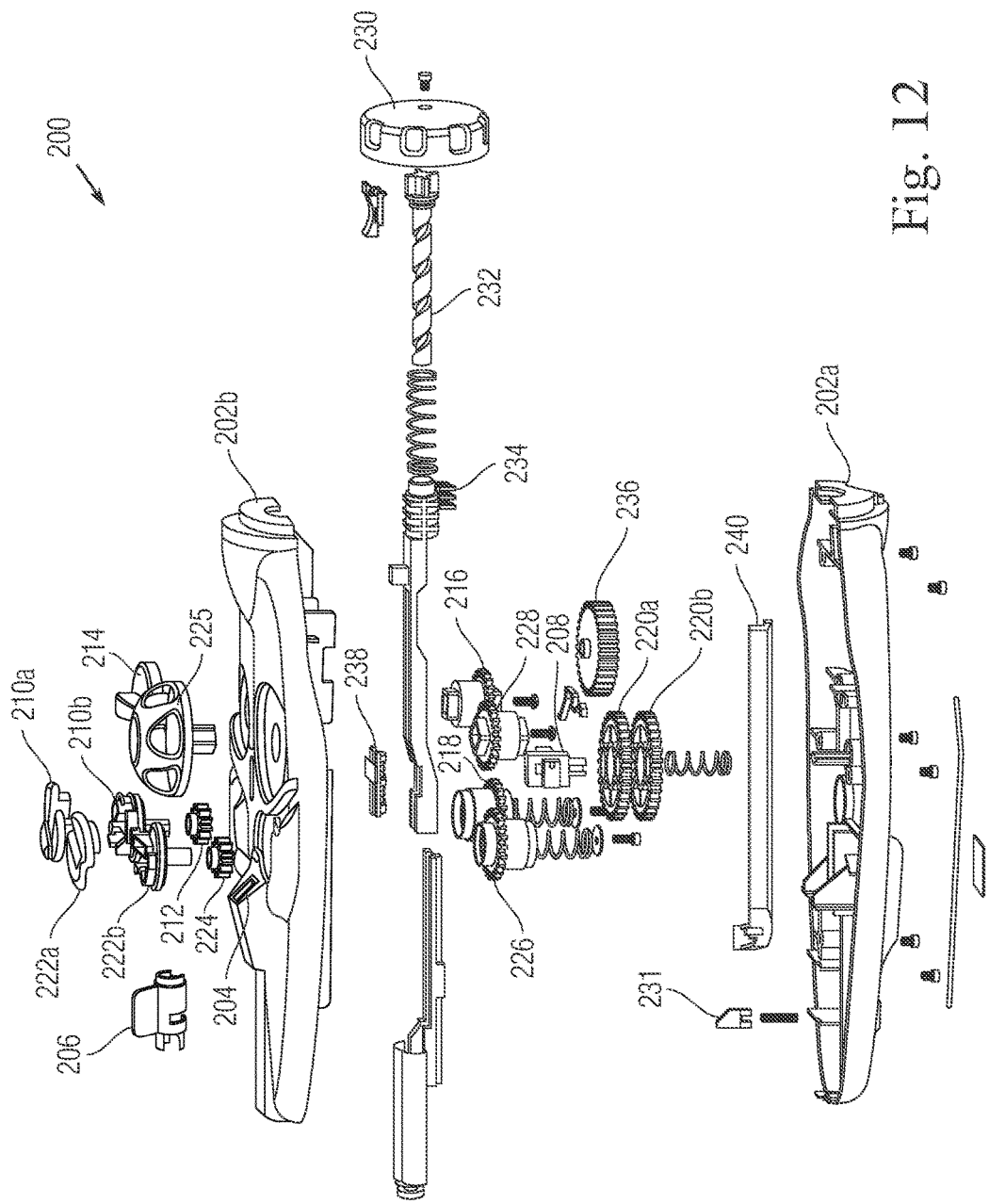
FIG. 12 is an exploded perspective view of an exemplary control assembly of a plication lock delivery system in accordance with the present teachings.

FIG. 12 illustrates an exemplary design of a control assembly (200) according to one embodiment of the present teachings. One skilled in the art should understand that other designs can also be used to achieve the functions described above and obvious variations thereof. Thus, what is illustrated and explained herein should not be construed as limiting. In this exemplary embodiment, the control assembly (200) includes a housing (202a, 202b). In some embodiments, the housing (202a, 202b) accommodates a suture tension mechanism, a tissue plication mechanism, and/or a lock deploy-and-release mechanism. In some embodiments, the housing (202a, 202b) also accommodates a suture port (204), a pre-load cam (206), a tension releasing means (208), and/or other parts or mechanisms.

In various embodiments, a pre-load cam is configured to have a ramp so that once the pre-load cam (206) is activated, it pushes the inner catheter distally while the pull wire and/or the outer sheath remain steady. As described above, in some embodiments, during pre-load configuration, an inner catheter of a catheter assembly is compressed by an outer sheath and the outer sheath is in tension by the inner catheter. In one embodiment, before activation, the pre-load cam (206) also functions to latch a suture threader in place. In certain embodiments, activating the pre-load cam also frees the suture threader and allow a suture to be threaded.

In various embodiments, a suture tension mechanism includes at least one of a top suture clamp (210a), a bottom suture clamp (210b), a clamp gear (218), a suture tension means (214), a suture tension gear (216), and a suture tension clutch (212). In some embodiments, once a suture is clamped between the top suture clamp (210a) and the bottom suture clamp (210b), a clinician starts the suture tension means (214) (rotatable knob), which engages and activates the suture tension gear (216). In certain embodiments, both the suture tension gear (216) and clamp gear (218) are connected to a center gear stack (220a, 220b) with a top gear (220a) and a bottom gear (220b). In certain embodiments, the motion of the suture tension gear (216) sets off a motion of the bottom gear (220b) of the center gear stack (220a, 200b), which in turn sets off the clamp gear (218). In certain embodiments, the motion of the clamp gear (218) allows a suture to be wrapped around the suture clamp (210a, 210b). In certain embodiments, a suture tension clutch (212) connected to the suture clamp (210a, 210b) is activated when a pre-defined tension is reached to prevent from over tensioning to the suture.

The suture clamps (210a, 222a) can include hinged lids that allow the user to observe and make sure that the suture is properly clamped to the clamp part. After the clamping is done, the lid is closed.

In various embodiments, a tissue plication mechanism includes at least one of a top suture clamp (222a), a bottom suture clamp (222b), a clamp gear (226), a tissue plication means (rotatable knob) (225), a tissue plication gear (228), and a tissue tension clutch (224). In various embodiments, once a suture is clamped between the top suture clamp (222a) and bottom suture clamp (222b), a clinician starts the tissue plication means (225), which engages and activates the tissue plication gear (228). In some embodiments, both the tissue plication gear (228) and clamp gear (226) are also connected to a center gear stack (220a, 220b). In some embodiments, the motion of the tissue plication gear (228) sets off a motion of the top gear (220a) of the center gear stack (220a, 200b). In some embodiment, the top gear (220a) of the center gear stack (220a, 220b) drives both the bottom gear (220b) and the clamp gear (226). In some embodiments, the motion of the clamp gear (226) allows a suture to be wrapped around the suture clamp (222a, 222b) and the bottom gear (220b) drives the suture tension gear (216) to prevent the other suture from losing its tension during tissue plication process. In certain embodiments, the suture tension clutch (224) connected to the suture clamp (222a, 222b) is activated when a pre-defined tension is reached, thereby preventing from over tensioning to the suture.

In various embodiments, a tension releasing means (208) is incorporated to reverse the suture tension. For example, a tension releasing means (208) pushes down the center gear stack (220a, 220b) so that clamp gears (226, 218) are freed. While no longer being strained, the sutures contract to lose its tension.

In various embodiments, a lock deploy-and-release mechanism includes at least one of a lock deploy-and-release means (230), a lead screw (232) connecting the lock deploy-and-release means (230), and a drive rack (234). During an exemplary lock assembly deployment, as the a lock deploy-and-release means (230) sets off, the lead screw (232) turns and the drive rack (234) pulls the pull wire (50) proximally since it is operatively coupled thereto. The motion of the drive rack also sets off a main drive gear (236), which then pushes the push arm (240) distally. The push arm (240) connects the proximal end of the outer sheath (48). A distal motion on the push arm will then drive outer sheath distally.

Figure 13:
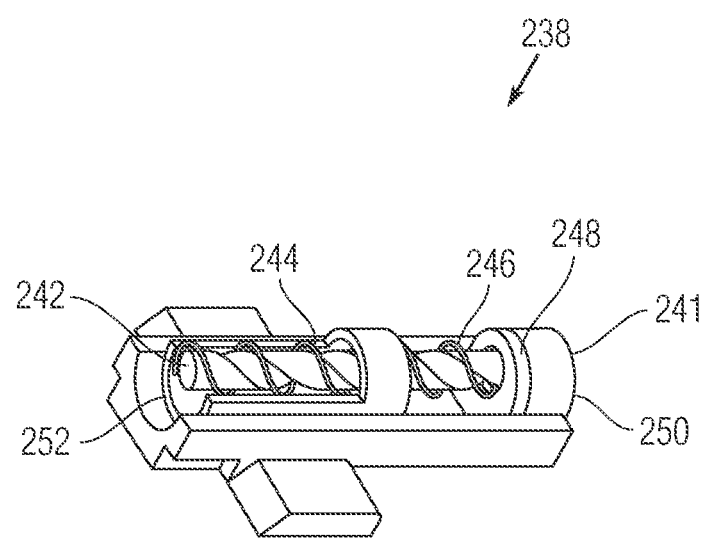
FIG. 13 is a perspective view of an exemplary pull wire clasp assembly in accordance with the present teachings.

In various embodiments, a control assembly includes a pull wire clasp assembly (238). The pull wire clasp assembly (238), as illustrated in FIG. 13, includes at least one of a clasp body (241), a barrel screw (242), a proximal spring (244), a distal spring (246), and a flat steel clasp (248). Referring to the embodiments illustrated in FIG. 13, the barrel screw (242) is threaded through the two springs (244, 246), the flat steel clasp (248), and the clasp body (240). In some embodiments, the distal end (250) of the barrel screw (240) connects the pull wire, for example, by thread or other means. A clasp (248) can include a hole which is able to slide over the barrel screw (242). The distal spring (246) can in turn slide over the barrel screw (242) and be positioned so that the spring (246) is compressed slightly, thereby pushing on the clasp (248) and causing it to cantilever relative to the barrel screw (242). In some embodiments, the proximal spring (244) slides over the barrel screw (242) and pushes proximally on the proximal end (252) of the barrel screw (242).

According to various embodiments of the present teachings, the clasp assembly (238) serve one or more functions. For example, the internal threads allow for enough adjustability of the pull wire (50) to the clasp assembly (238) joint to ensure that the relative lengths of the inner catheter (46) and pull wire (50) are always normalized appropriately for assembly. For example, the proximal spring (244), which pushes with a load on the barrel screw (242), ensures that the pull wire is always under a predetermined load during packaging and handling of the device. For example, the compressed proximal springs (244) take up any pull wire slack that may occur during normal use of the plication and lock delivery system and makes sure that the pull wire is always under some predetermined minimum amount of tension so that lock assembly is not released prematurely. The pull wire clasp assembly can be used as a one-way clasp. In some embodiments, a flat steel clasp (248) component, which is biased by a distal spring (246), allows the barrel screw (242) to migrate proximally, but locks any proximal motion in place. In these embodiments, the flat steel clasp (248) component completely prevents any distal migration of the barrel screw (242). In some embodiments, the locking feature of the clasp functions because the cantilevered nature of the clasp and the tightly controlled diameter of the hole in the clasp conspire to create a jamming effect when tension is apply distally to the barrel screw (242). For example, the higher is the distal tension force on the barrel screw (242), the more cantilevered becomes the flat steel clasp (248) and the harder it binds on the barrel screw (242).

In various embodiments, after a predetermined distance, for example, about 5 mm, of the lock deployment (measured by the travel distance of drive rack), the inner catheter is released, for example, by releasing a pre-load keeper (231), such that the inner catheter does not restrict a proximal movement of the lock body.

In various embodiments, the total drive rack motion given to a lock assembly deployment is approximately 18 mm. After this distance, for example, a pull wire clasp assembly (238) engages into a stationary alcove so that it is not pulled any father. At approximately the same time, the drive rack (234) can disengage from the drive gear (236) (by disengagement of teeth of the rack from teeth of the gear) and allow the outer sheath push arm (240) to return to the unload position and release the load on the outer sheath. The alcove is formed within an underside of the housing (202b). The pull wire clasp assembly (238) is received within a track formed in the drive rack (234) and as the drive rack is driven, the pull wire clamp assembly (239) is carried by the drive rack (234). In FIG. 12, the track is shown directly below the assembly (238). Once the clasp assembly (238) is in registration with the alcove, the assembly (238) is received into the alcove and thereby is disengaged from the rack (234). The drive rack (234) can continue to move longitudinally without carrying the clasp assembly (238).

In various embodiments, when a lock assembly deployment is completed, a ramp on the drive rack (234) is pushed down on the suture lease button to cause the tension on both the sutures to be released. In some embodiments, after all of the tension is released, the drive rack (234) engages with the inner catheter hub and the remainder of the travel is used to pull the inner catheter proximally. This motion can pull the distal post of the inner catheter out of the lock body and allow the pull wire to be released from the lock body. At this point, the catheter assembly is no longer attached to the lock assembly and can be removed from the body.

While the devices are discussed at length for being used to plicate a mitral valve annulus and deliver a plication lock, it should be understood and appreciated that the devices of the present teachings can be used in other applications related and unrelated to the mitral valve repair. For example, some embodiments of the present teachings can be used to close and secure an unwanted opening in a tissue in the body, such as the stomach, and to repair another dysfunctional valve in the heart, such as the tricuspid valve.

The control system (60) of the present invention thus allows the user to perform a number of different operations. For example and as described herein, in a pre-load position, the sutures can pass through the catheter lumen and through the lumen (26) of the lock body (30) and are not locked in place. The loop (52) at the end of the pull wire (50) is disposed around the protrusion (43) which itself is disposed within blind hole (35), thereby coupling the inner catheter to the lock body. The ends of the pin (32) are received within the slots (J shaped) (55) formed within the interior of the outer catheter (48), thereby coupling the lock body (30) to the outer catheter. In this position, the pull wire (50) can move separate and independent from the inner catheter (46) (i.e., the pull wire 50 can be pulled as by action at the control system to cause longitudinal movement thereof (i.e., pull wire (50) can be pulled). As described herein, the user uses the control system (60) to apply tension to the sutures (16, 18) as part of a tissue plication step. This is done using the respective controls that are part of the control mechanism (60). As described, to lock the locking body, the mechanism (70) is rotated and this causes the pull wire (50) to move in a proximal direction (toward the mechanism 70) and since the pull wire loop is engaged with the post (43), the inner catheter (46) likewise moves proximally. Simultaneously, this user action results in the outer catheter (48) being driven distally. These two key parts (assemblies) are thus moving in opposite directions resulting in the pin (32) moving within slot (38) (and moving within the slot (55) into a locking position in which the pin (32) contacts and pinches the sutures (16, 18) to lock them in place. Further manipulation (further rotation) at the control system (70) results in the undocking of the inner catheter (46) from the lock body (30) as a result of the post (43) disengaging from the blind hole (35). This action allows the loop (52) and pull wire (50) to be pulled from the side channel (37) since the post (43) no longer passes through the loop (52). Also, the pin (32) continues to move in the slot (55) and slides laterally and disengages from the slot (55), thereby disengaging the lock body from the outer catheter, while still maintaining a lock of the sutures (16, 18) due to the location of pin (32) in the slot (38). The lock assembly (20) is thus released and left at the site with the sutures locked in place.

Unless otherwise defined, all technical and scientific terms used herein have the same meaning as commonly understood by one of ordinary skill in the art. Methods and materials similar or equivalent to those described herein can be used in the practice or testing of the present teachings. In case of conflict, the patent specification, including definitions, will control. In addition, the materials, methods, and examples are illustrative only and not intended to be limiting.

We claim:

1. A plication lock delivery system for creating a tissue plication comprising:
a lock assembly comprising a lock body and a lock pin, wherein the lock body has a central lumen configured to retain the lock pin and to have a first suture and a second suture disposed within the central lumen;
a catheter assembly comprising an outer sheath and an inner catheter, wherein the inner catheter has a distal end, a proximal end, and a central lumen, wherein the distal end of the inner catheter is configured to detachably connect to the lock body, wherein the central lumen is configured to have the first and the second sutures disposed within, wherein the outer sheath has a distal end and a proximal end, wherein the distal end is configured to contact the lock pin and cause movement thereof; a first suture tension mechanism configured to apply tension to the first suture; and
a second suture tension mechanism configured to apply tension to the second suture
wherein a control assembly is operatively coupled to the proximal ends of the outer sheath and inner catheter;
wherein the lock body further includes a first locking slot formed therein and extending along a longitudinal length thereof, the first locking slot intersecting the central lumen in which the first and second sutures are located, the lock body further including a side opening that is open along a side thereof and communicates with the central lumen and a second opening that is open at a proximal end of the lock body, the second opening being spaced and separate from the longitudinal lumen wherein the side opening intersects and passes through the second opening;
wherein a locking pin extends through the first locking slot with ends of the locking pin being disposed outside of the lock body, the ends being received in a complementary second locking slot that is formed along the inner surface of the outer sheath, thereby coupling the lock body to the outer sheath.

2. The system of claim 1, wherein the inner catheter includes a post that extends outwardly from the distal end of the inner catheter, the post being received within the second opening for detachably connecting the inner catheter to the lock body.

3. The system of claim 2, further including a pull wire that is operatively connected at a proximal end to the control assembly such that the pull wire can be controllably pulled in a proximal direction by operation of the control assembly and independent from longitudinal translation of the inner catheter, the pull wire having a loop formed at a distal end thereof, wherein the loop is disposed within the side opening with the post passing through an opening of the loop when the lock body is connected to the inner catheter.

4. The system of claim 1, wherein each of the first and second suture tension mechanisms includes a suture clamp device to which the respective suture is attached, a suture tensioning actuator and a suture tension gear coupled to the suture clamp device such that operation of the suture tensioning actuator causes rotation of the suture tension gear and rotation of the suture clamp device resulting in a winding of the suture about the suture clamp device and tension being applied to the suture.

5. The system of claim 4, wherein each suture tension mechanism includes a clutch that is operatively connected to the suture clamp device such that once a predefined tension in the suture is achieved, the clutch is activated to prevent the suture from being over tensioned.

6. A method of plicating a tissue and securing the tissue plication with a lock assembly percutaneously comprising:
providing a plication lock delivery system with a lock assembly, a catheter assembly comprising an outer sheath and an inner catheter, and a control assembly, wherein the lock assembly comprises a lock body and a lock pin, wherein the lock body has a central lumen configured to retain the lock pin and has a first and a second suture disposed within, the lock body further including a first locking slot formed therein and extending along a longitudinal length thereof that intersects the central lumen in which the first and second sutures are located, a side opening that is open along a side thereof and communicates with the central lumen and a second opening that is open at a proximal end of the lock body, the second opening being spaced and separate from the longitudinal lumen wherein the side opening intersects and passes through the second opening, and the lock pin extends through the first locking slot with ends of the lock pin being disposed outside of the lock body, the ends being received in a complementary second locking slot that is formed along the inner surface of the outer sheath, thereby coupling the lock body to the outer sheath, the inner catheter having a distal end, a proximal end, and a central lumen, and wherein the distal end of the inner catheter is configured to connect to the lock body, the central lumen being configured to have the first and the second sutures disposed within, and the outer sheath having a distal end configured to contact the lock pin and a proximal end; and wherein the control assembly connects the proximal ends of the outer sheath and inner catheter and comprises a first suture tension mechanism configured to apply tension to the first suture and a second suture tension mechanism configured to apply tension to the second suture;
extending the first and second sutures through the lock assembly;
extending the first and second sutures from the distal end to the proximal end of the catheter assembly;
applying tension to the first suture with the first suture tension mechanism of the control assembly;
applying tension to the second suture with the second suture tension mechanism of the control assembly;
securing the first and the second sutures to the lock assembly with a lock deploy-and-release mechanism of the control assembly; and
releasing said lock assembly from the catheter assembly.

* * * * *